(12) United States Patent
Frankfort et al.

(10) Patent No.: US 9,220,405 B2
(45) Date of Patent: Dec. 29, 2015

(54) SYSTEM AND METHOD FOR EVALUATING OCULAR HEALTH

(71) Applicant: Baylor College of Medicine, Houston, TX (US)

(72) Inventors: Benjamin J. Frankfort, Houston, TX (US); Cameron S. Cowan, Houston, TX (US); Samuel Miao-sin Wu, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 0 days.

(21) Appl. No.: 14/622,308

(22) Filed: Feb. 13, 2015

(65) Prior Publication Data
US 2015/0150443 A1    Jun. 4, 2015

Related U.S. Application Data

(63) Continuation of application No. 13/732,959, filed on Jan. 2, 2013, now Pat. No. 8,992,019.

(60) Provisional application No. 61/584,050, filed on Jan. 6, 2012.

(51) Int. Cl.
*A61B 3/14*    (2006.01)
*A61B 3/00*    (2006.01)
*A61B 3/113*   (2006.01)

(52) U.S. Cl.
CPC ............. *A61B 3/0025* (2013.01); *A61B 3/0091* (2013.01); *A61B 3/113* (2013.01)

(58) Field of Classification Search
CPC ...... A61B 3/113; A61B 3/032; A61B 3/0091; A61B 5/4863
USPC .......................... 351/205, 209–211, 221, 239
See application file for complete search history.

(56) References Cited

U.S. PATENT DOCUMENTS

| | | |
|---|---|---|
| 5,912,723 A | 6/1999 | Maddess |
| 7,918,558 B1 | 4/2011 | Legerton et al. |
| 2007/0106751 A1 | 5/2007 | Moore |
| 2012/0276127 A1 | 11/2012 | Adamus et al. |

OTHER PUBLICATIONS

Prusky, et al., "Rapid Quantification of Adult and Developing Mouse Spatial Vision Using a Virtual Optomotor System", Investigative ophthalmology & Visual Science, Dec. 2004, vol. 45, No. 12, pp. 4611-4616, Association for Research in Vision and Ophthalmology.

(Continued)

*Primary Examiner* — Mahidere Sahle
(74) *Attorney, Agent, or Firm* — Norton Rose Fulbright US LLP

(57) ABSTRACT

A method for adaptively determining a model of visual performance of a test subject comprising the step of exposing a test subject to a plurality of trials. Each trial comprises the steps of identifying the stimulus pattern to test, generating a stimulus pattern on a display, determining whether the stimulus pattern generated an OKR, updating the model to incorporate the OKR results, and determining whether the updated model is acceptable. The trials can be iteratively repeated until the model for visual performance is acceptable.

46 Claims, 11 Drawing Sheets

(56) References Cited

OTHER PUBLICATIONS

Burroughs, et al. "Quantification of deficits in spatial visual function of mouse models for glaucoma", IOVA Papers in Press. Published on Feb. 17, 2011 as Manuscript iovs.10-7106, The Association for Research in Vision and Ophthalmology, Inc., 2011.

Cahill, et al., "The Optokinetic Reflec as a Tool for Quantitative Analyses of Nervous System Function in Mice: Application to Genetic and Drug-induced Variation", Apr. 30, 2008, PL0S ONE, vol. 3, Issue 4, e2055, doi:10.13714/journal.pone.0002055.

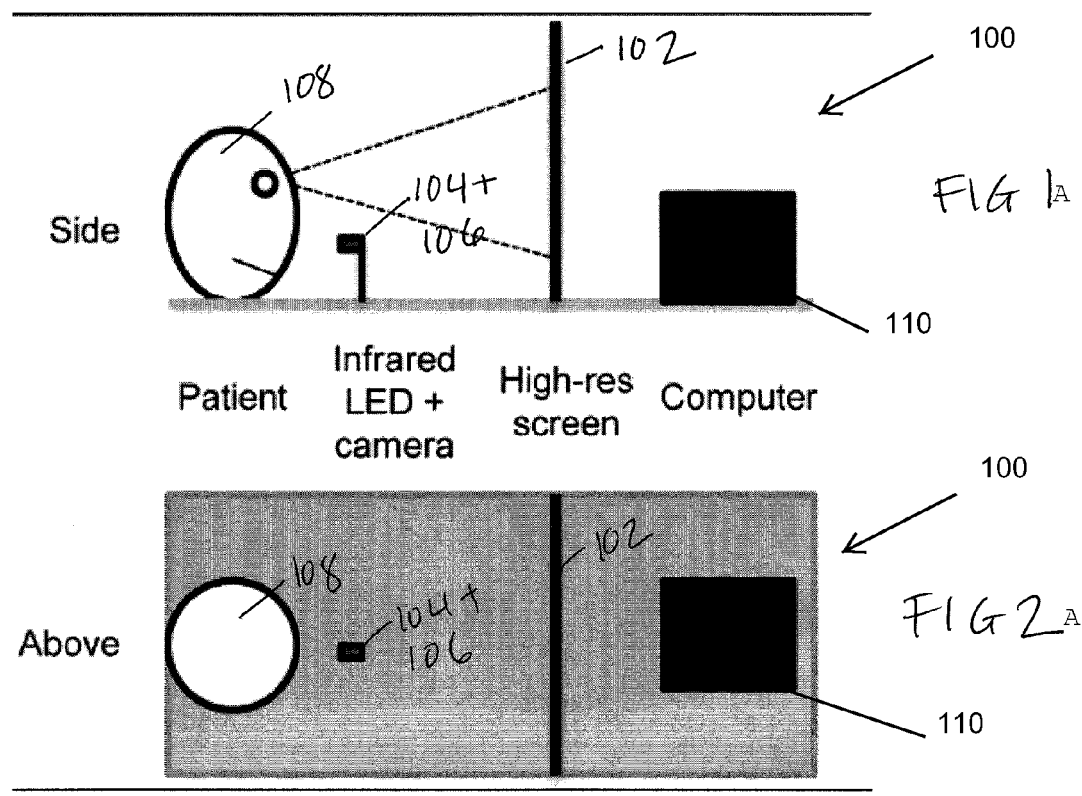

Side | Patient | Infrared LED + camera | Rotatable Opaque Divider | High-res screen | Computer 108, 102, 118, 100, 110

Above 108, 102, 100, 110

SYSTEM AND METHOD FOR EVALUATING OCULAR HEALTH

CROSS-REFERENCE TO RELATED APPLICATIONS

This is a continuation application of U.S. patent application Ser. No. 13/732,959 previously filed on Jan. 2, 2013 entitled SYSTEM AND METHOD FOR EVALUATING OCULAR HEALTH which claims the benefit of priority to U.S. Provisional Application No. 61/584,050 filed Jan. 6, 2012 entitled SYSTEM AND METHOD FOR EVALUATING OCULAR HEALTH, both of which are herein incorporated by reference in their entirety.

TECHNICAL FIELD

The present invention is related to a method for testing visual capacity and, more particularly, to a noninvasive system and objective method for analyzing retinal function for a multiplicity of different purposes.

BACKGROUND OF THE INVENTION

Optokinetic nystagmus (OKN) or Optokinetic Reflex (OKR) is the rhythmic movement of the eyes when tracking a moving field. In particular, OKN can be induced by presenting a test subject with a drifting image of sinusoidally modulated gratings, where the eye experiences a slow or smooth phase in which the eye reflexively tracks the stimulus alternating with a saccadic or fast phase in which the eye rapidly re-fixates in the opposite direction and then begins to track again.

By adjusting the characteristics of the drifting image, contrast sensitivity thresholds and visual acuity of a test subject can be measured. These measurements are somewhat subjective because they require either responses from the test subjects themselves (e.g., when a visual cue is detected or not) and/or interpretation of the test subject's eye movements by the operator. The required inputs by the test subjects and/or operator can vary among tests, subjects, and operators, which pose challenges to physicians in deciphering, interpreting, and sharing test results for use in various purposes, such as diagnosis or academic research. Moreover, conventional tests are not particularly applicable to test subjects who are not able to understand or communicate detection of visual cues. In addition, conventional tests typically take a relatively long time to perform, e.g., 20-30 minutes or much longer depending on the test, which is an inconvenience for both the patient and the operator.

Further, conventional testing of visual function is generally done under "normal" lighting conditions (i.e., bright light). This is typically for convenience purposes because testing of visual function under different lighting conditions requires a readjustment period between one condition and the next before testing can take place. For instance, before a patient's visual function can be tested in a dark room, the patient must be placed in the dark room for about 15 minutes to allow their eyes to adjust to the dim or dark conditions. This readjustment is often called dark adapting or dark adaptation, and it is done to test the function of the rod photoreceptors, which are more sensitive to light than cone photoreceptors and the dominant detectors of light under dark conditions. They are saturated in bright light, so the less sensitive cone photoreceptors dominate in conventional testing conditions of bright light. Thus, conventional tests generally measure cone photoreceptors only. Along the same lines, once the subject has been in the dark for a while, the stimulus presented also has to be dimmer because a "normal" brightness will end up testing the less sensitive cones by supersaturating the rods. A less bright stimulus is too dim for the less sensitive cone photoreceptors to detect but perfect for the sensitive rod photoreceptors. Conventional tests are not applicable for darker testing conditions because they do not make brightness adjustments to account for testing of the rods.

Therefore, there is still a need for a method for testing visual capacity which reliably permits the objective testing of a test subject; which has application to human beings, animals such as mammals, and other forms of life; which achieves a degree of reliability significantly enhanced over that heretofore achieved in the art; which can be employed for the purpose of directly testing contrast sensitivity and/or visual acuity of the test subject as well as testing for a multiplicity of other physical conditions that may be evidenced, or otherwise evaluated, based on the contrast sensitivity and/or visual acuity of the test subject; which can be employed, more generally, in a multiplicity of environments wherein it is desirable, or of importance, to know the contrast sensitivity and/or visual acuity of the test subject without compromise or influence by subjective considerations; which is comparatively inexpensive to employ while being adaptable to virtually all operative environments such as lighting conditions; and which is otherwise entirely suited to achieving its operational objectives, and which can be completed in a short amount of time.

Traditional retinal function tests have difficulty testing for early detection of glaucoma, age related macular degeneration, and other similar eye diseases such as cataract and retinal dystrophy, for diagnosing malingering, and for vision testing in non-communicative patients, such as infants, toddlers, patients with neurological deficits or cognitive disorders, and animals.

SUMMARY OF THE INVENTION

An objective measurement of contrast sensitivity that invokes an optokinetic response (OKR) with a moving sinusoidal grating whose parameters (contrast and spatiotemporal frequency) are adaptively chosen by a machine learning algorithm optimized to rapidly determine the patient's visual performance.

According to one embodiment of the present disclosure, patient responses relating to whether or not a visual cue is detected are not required. In another embodiment, operator interpretation of the patient's responses or physical movement, e.g., eye movements, is not required. Accordingly, some embodiments of the present disclosure provide objective results and analysis and can be used on non-communicative patients, including but not limited to stroke victims, preverbal children, patients suffering from dysphasia, congenital deafness, severe depression, motor retardation, Alzheimer's disease, any disease causing motor tremor, arthritis of any form, weakness of any form, or inattention of any form. Other embodiments that provide objective results can be used to test the vision of various animals, including but not limited to mice, rats, rabbits, guinea pigs, dogs, and monkeys, such as during drug trials.

Examination of the visual capacity of the patient according to some embodiments of the present disclosure can be achieved rapidly, preferably about one minute per eye. Some embodiments of the present disclosure can be used to evaluate visual capacity under all lighting conditions (e.g., light, dim, dark). Some embodiments of the present disclosure can be used to evaluate all retinal sensitivity states (e.g., photopic, mesopic, scotopic).

Some embodiments provide automated and direct comparison of inter-ocular responses (right vs. left eye). Yet other embodiments provide automated and direct comparison of intra-ocular responses (light vs. dim vs. dark vs. direction of stimulus in one eye). Additional embodiments provide automated and direct comparison of both inter-ocular and intra-ocular responses to previous testing results obtained by the same patient at an earlier date or dates, such as to monitor changes or fluctuations over time.

Other embodiments can be used to determine the sensitivity of the patient's response to contrast, spatial frequency, temporal frequency, and/or speed.

Other embodiments can be used to determine the critical values/gain of contrast sensitivity, spatial acuity, temporal acuity, and/or speed facility.

Some embodiments provide greater accuracy and speed over the conventional methods by employing an adaptive machine learning algorithm to choose at least the starting stimuli to be used in testing a patient. As such, some embodiments do not follow a stepwise or fixed testing algorithm in changing the visual cues.

In one embodiment, the adaptive algorithm incorporates population statistics as an input to inform both the experimental protocol and data interpretation.

Some embodiments provide rapid identification of pupil position and movement through use of infrared illumination and integrated software.

Some embodiments use display devices and supporting hardware capable of presenting images with high bit depth, dynamic range, and ANSI contrast ratio.

Some embodiments address dynamic range limitations of certain monitors or display devices by using wavelength-neutral density filters to dim the monitors, thereby allowing the image to be presented in a lower-gain intensity range.

Some embodiments provide for administration of constantly changing stimuli with immediate feedback to further streamline testing.

The present disclosure allows for multiple testing paradigms to optimize for specific ocular diseases.

The embodiments of the present disclosure may be used in one or more of the following applications, which are listed for illustrative purposes and are not intended to limit the scope of the present disclosure: (1) identification of glaucoma of all forms; (2) monitoring of changes in glaucoma of all forms; (3) determination of change in visual function after glaucoma surgery or glaucoma laser surgery; (4) determination of change in visual function after use of glaucoma medications; (5) monitoring of cataracts of all forms; (6) screening for refractive surgery; (7) screening for multifocal intraocular lens implantation; (8) determination of change in visual function after cataract surgery; (9) determination of change in visual function after refractive surgery; (10) determination of visual function in macular degeneration of all forms; (11) determination of change in visual function after treatment of macular degeneration; (12) determination of visual function in diabetic retinopathy; (13) determination of change in visual function after treatment of diabetic retinopathy; (14) determination of visual function in disease states of the cornea; (15) determination of visual function after retinal arterial or vein occlusion; (16) determination of visual function in optic neuritis or any genetic or acquired disease of the optic nerve; (17) determination of non-organic visual loss (malingering, psychiatric disease); (18) determination of visual function in instances of genetic or acquired disease of the brain; and (19) confirmation of subjective measurement of visual function in any patient.

According to one embodiment, a method for determining a visual performance metric of a test subject, said method comprising the steps of estimating, by a processor, a model for at least one visual performance metric; identifying, by the processor, a test pattern based, at least in part, on the estimated model; generating, on a display, the test pattern to present the test pattern to the test subject; determining, by the processor, an Optokinetic Reflex (OKR) result indicating whether the test pattern induced OKR in the test subject; updating, by the processor, the model to incorporate the OKR result; and determining, by the processor, whether the updated model is acceptable.

According to another embodiment, a method for determining a visual performance metric of a test subject, said method comprising the steps of exposing the test subject to a plurality of trials, wherein each trial comprises the steps of: estimating, by a processor, a gain value for a visual performance metric; generating, by the processor, a test pattern based, at least in part, on the gain value; presenting, by a display, the test pattern to the test subject; determining, by the processor, whether the test pattern induced Optokinetic Reflex (OKR) in the test subject; and determining, by the processor, whether the gain value is acceptable.

According to yet another embodiment, an apparatus includes a display, a memory, and a processor coupled to the memory and to the display. The processor is configured to estimate a model for at least one visual performance metric, identify a test pattern based, at least in part, on the estimated model, generate the test pattern to present the test pattern to the test subject, determine an Optokinetic Reflex (OKR) result indicating whether the test pattern induced OKR in the test subject, update the model to incorporate the OKR result, and determine whether the updated model is acceptable.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention.

FIG. 1A illustrates a side view of a system to evaluate visual capacity in accordance with one embodiment of the present invention.

FIG. 2A illustrates a top view of the system in FIG. 1A.

DETAILED DESCRIPTION OF THE EMBODIMENTS

Figure 1B:
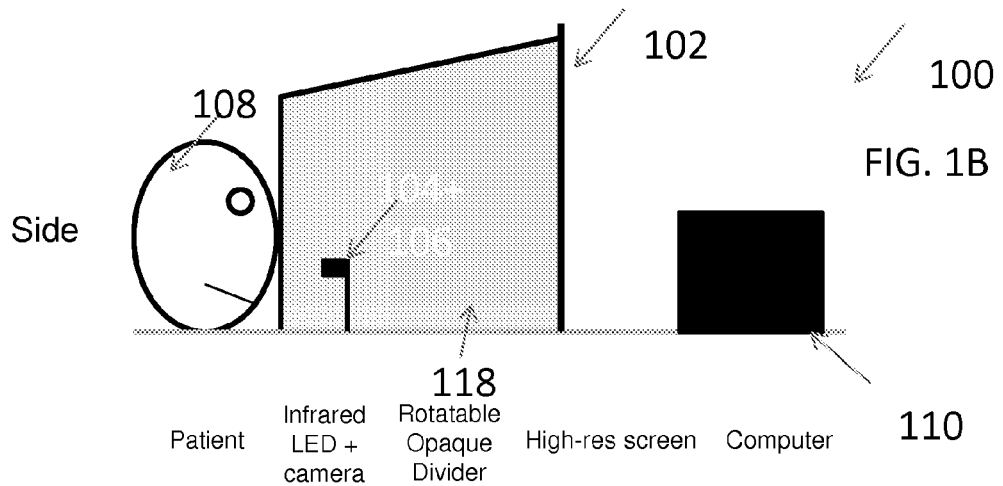
FIGS. 1B and 2B illustrate an alternate arrangement of a system to evaluate visual capacity in which testing is restricted to one eye at a time through the use of a rotatable opaque divider for use with certain embodiments of the present disclosure.

The present invention is directed toward a system and method for providing a visual system diagnostic test. A visual stimulus is presented to a patient to induce the optokinetic nystagmus (OKN) or optokinetic reflex (OKR) response in the patient. Various parameters of the stimulus are modified to probe the patient's visual function (in terms of OKN sensitivity) and estimate their level of visual performance based on a variety of parameters. This estimate of visual performance can provide diagnostic information about contrast sensitivity, spatial acuity, temporal acuity, speed, or visual or retinal system functioning for patients of all types, including non-verbal humans or animals that would otherwise be unable to be diagnosed.

FIGS. 1A and 2A illustrate a testing system 100 according to an embodiment of the disclosure, which includes at least a display device 102, an illuminating device 104, and a camera 106. Patient 108 is presented with a visual stimulus 112 in FIG. 3 displayed on a display device 102 such as a high-resolution screen, which is typically digital but can be analog. Preferably, the patient places his/her chin and forehead on a vertically adjustable positioning rest (not shown) that is aligned with the high resolution digital screen 102, illuminating device 104, and pupil-monitoring camera 106. The system 100 also preferably has a chin/head rest (not shown) to provide support to the head of the patient 108 and allow for placement and adjustment of head position with respect to the display device 102. The system 100 also preferably is mounted on an adjustable table such that the distance from the floor can be either increased or decreased to maximize patient 108 comfort. The patient 108 is preferably seated in a chair that is adjustable at least in the vertical direction. The illuminating device 104 is preferably one or more infrared LEDs that is located near the camera 106 to provide the necessary lighting.

The camera 106 is a black and white model with a charge coupled detector (CCD) detector that is able to recognize light in the infrared spectrum. The camera 106 also contains a filter that blocks out light with a wavelength shorter than infrared to prevent interference from light generated by the display device 102. For most purposes, a camera 106 recording speed of 60 frames per second at a resolution of 640×480 is acceptable, although improvements in both recording speed and resolution reduce noise in the recordings and can improve results. In some embodiments, a macro lens may be used to allow for camera 106 placement close to the eye. Illumination source 104 intensity levels and wavelengths should be chosen with respect to the light collection capabilities of the optics and wavelength sensitivity of the camera's 106 CCD, respectively. The display device 102 is preferentially digital, with a wide dynamic range and a high bit value color look-up table (10 bit+). In the preferred embodiment, the monitor will be able to display greater than the typical 8 bits of grayscale resolution. The camera 106 is preferably placed below patient 108 eye level at the greatest height possible that does not obstruct the patient's view of the screen. To maximize light collection, it is preferred for the camera 106 and illumination source 104 to be placed within 16 inches of the patient's 108 eye.

Figure 2B:
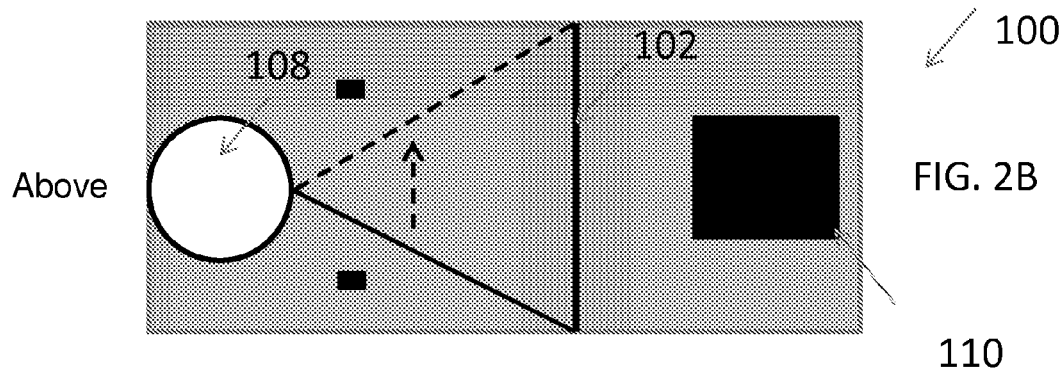
Figure 3A:
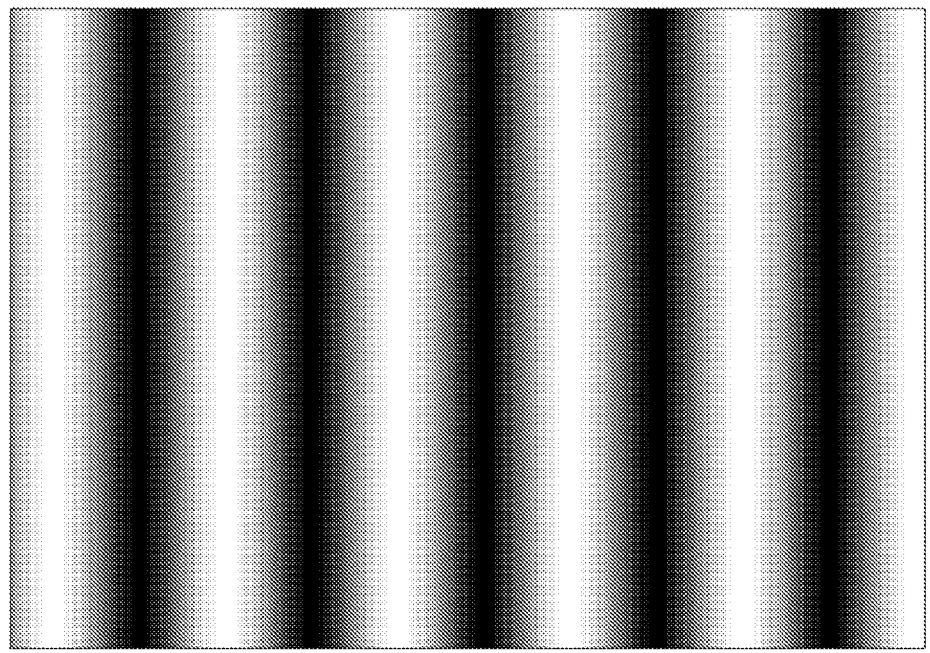
FIG. 3A illustrates an exemplary visual stimulus according to the aspects of the present disclosure.
Figure 3B:
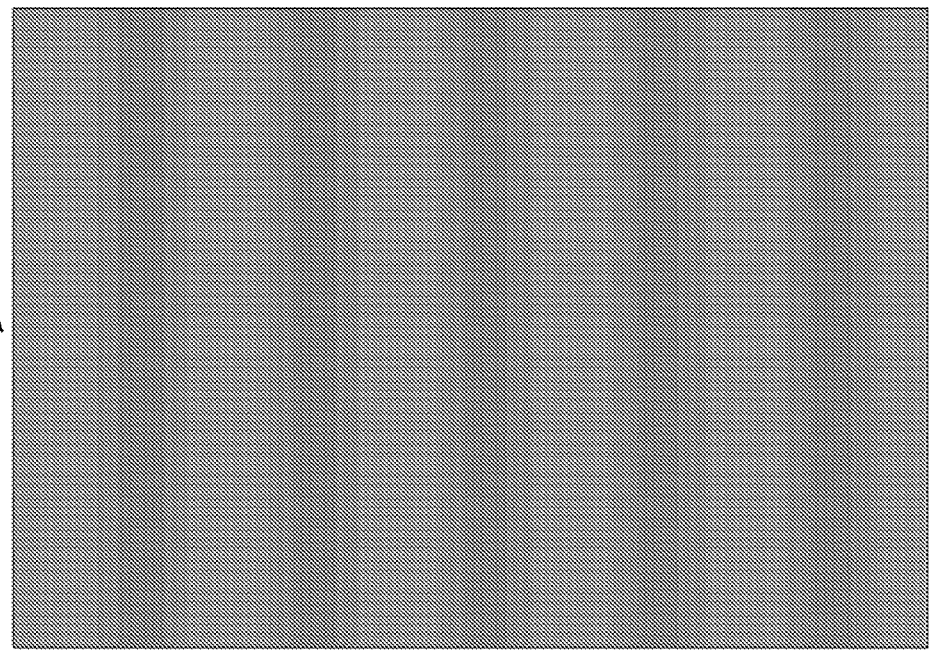
FIG. 3B illustrates an exemplary visual stimulus comprising low contrast sinusoidal gratings according to the aspects of the present disclosure.

The display device 102, illuminating device 104, and camera 106 are preferably coupled to a computer system 110 that can control the visual stimuli being presented to the patient 108, monitor and record the responses of the patient 108, and analyze the data recorded. The camera 106 is preferably located near the eye of the patient 108 as described above. In another embodiment, there is an additional camera, one for each eye so there would be no need to move the camera when the other eye is tested (described below). In embodiments with two cameras, there is preferably an additional illuminating source associated with the second camera, similar to illuminating source 104, to provide sufficient lighting for the camera to capture images of the eye. In another embodiment, a one or two camera system is used in order to accommodate a rotatable opaque divider that allows for isolation of one eye at a time during testing, as shown in FIGS. 1B and 2B. The camera 106 is capable of capturing the movements of a patient's pupil in video format as commanded by the computer system 110. In one embodiment, visual stimulus 112 is presented to the patient 108 on display device 102.

Figure 5:
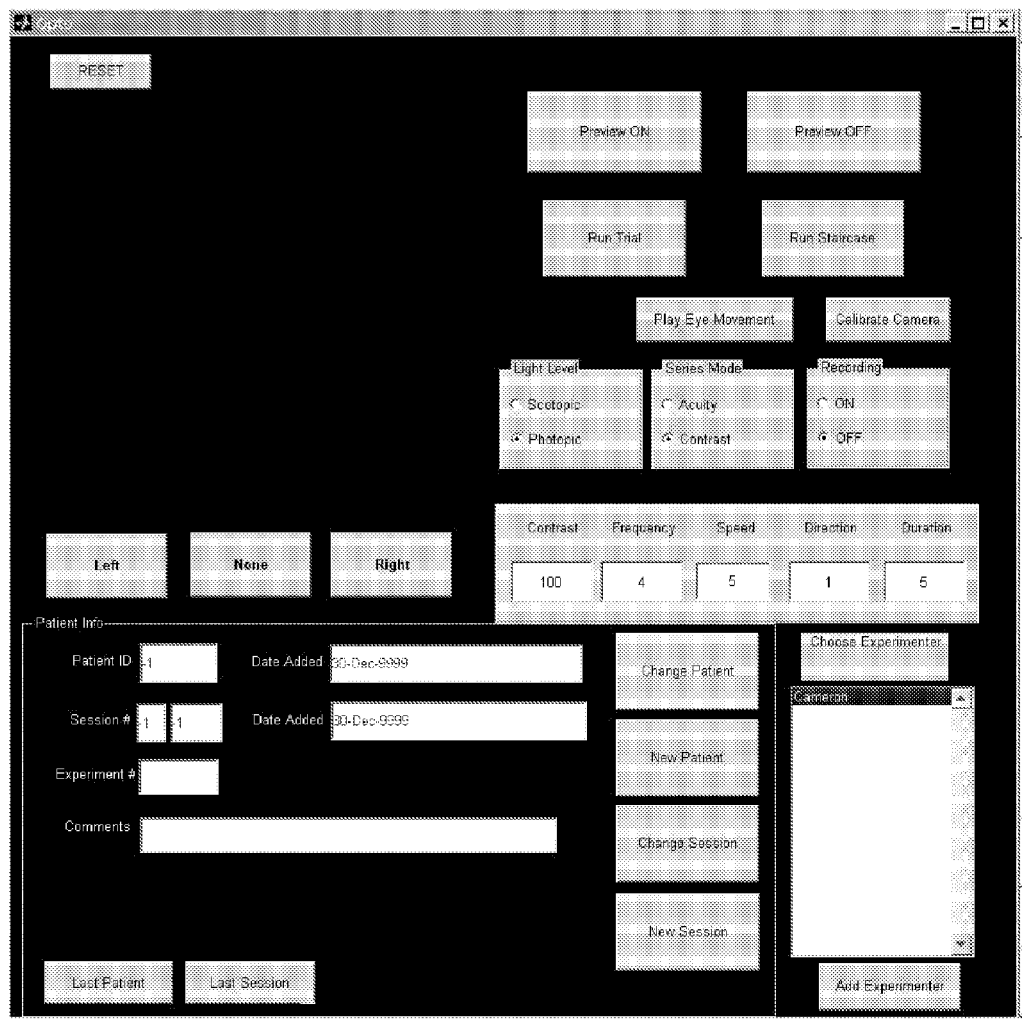
FIG. 5 illustrates an exemplary embodiment of a user interface according to the aspects of the present disclosure.

The platform on which the display device 102 rests can be vertically adjustable for comfort. The testing system 100 can further include a user interface, preferably presented on a separate display device, such as a computer monitor separate from display device 102, to allow the operator to control the testing system 100, including initiating a test, capturing images of a patient's pupil, performing quality control, and analyzing the data. FIG. 5 illustrates an exemplary embodiment of a user interface of the present disclosure. In other embodiments, the user interface can be presented to a remote display that is a handheld device, such as a Smartphone, PDA, laptop, desktop, or tablet or other similar devices. This allows for wireless operation of system 100. In one embodiment, the separate display device (not shown) coupled to the computer system 110 (via wires or wirelessly) can show the images of the patient's pupil provided by the camera 106. This allows for confirmation of proper head and eye positioning within the device along with feedback showing pupil tracking is working. In another embodiment, the separate display device can present analysis of the test results immediately after completion for documentation and can be coupled either directly or remotely to a printer to provide a hard copy of results and directly and/or to a data storage device for storing the test results.

The display device 102 is preferably a high resolution screen with high dynamic range and ANSI contrast ratio, which can provide the ability to present and test very small gradations of contrast accurately. In one embodiment this is achieved by use of specialized digital monitors with high bit depth color look-up tables. In an alternative embodiment, bit depth conversion hardware can be used to achieve high bit depth stimuli using off the shelf monitors and computers. In one embodiment this hardware would attenuate and combine tri-color RGB signals to generate grey scale images with increased bit depth. In an alternative embodiment, digital signals from multiple video outputs would be combined to form a single high bit depth image. The computer 110 can be equipped with a video card, operating system, video drivers, and other software capable of generating high bit depth images in that embodiment. These high quality images can allow for accurate testing of individuals that have excellent contrast sensitivity, spatial acuity, temporal acuity, and/or speed facility typically in a healthy eye. Otherwise, the contrast sensitivity, spatial acuity, temporal acuity, and speed facility can be beyond the testing capacity of lower color depth screens, which would result in an imprecise determination of visual performance.

Alternatively, consumer grade monitors or other monitors that may not have the color depth properties discussed above can be used as is. Wavelength-neutral density filters can be placed either across the face of the monitor or at another position between the observer's eyes and the screen to make visual performance more difficult and thereby improve the testing range of these monitors. The filters allow for more precise determination of visual performance in healthy patients.

Visual stimulus 112 preferably comprises a plurality of parallel sinusoidally modulated contrast gratings. The preferred case is vertically-oriented sinusoidal gratings, and the alternative case includes horizontally-oriented sinusoidal gratings or more complicated arrangements such as radially-oriented sinusoidal gratings. Another alternative case (the simplest case) includes maximally contrasted sinusoidal gratings. The sinusoidal grating can comprise any shade of gray, depending on the parameters determined by the testing system 100. The testing system 100 can provide stimuli that translate in a leftward or rightward direction on the display device 102 by incrementally increasing or decreasing the phase of the sinusoid between frames. This apparent motion induces the OKN response in the patient 108. In addition to the contrast of the gratings, the testing system 100 can adjust the width (or spatial frequency) and temporal frequency of the visual stimuli. In addition, the visual stimuli can be "frequency chirped" by the testing system 100 to create the effect of making the observer feel like he/she is watching a cylinder with a sinusoid painted on it, i.e., an illusion of a curved surface, rather than watching a flat moving wall with a sinusoid painted on it.

In some embodiments, other parameters of visual stimulus 112 can be modified. For example, the gratings can have increased or reduced width and/or height, elements having a range of contrasts and elements having different colors, hues, or shades.

Various embodiments may also employ different test patterns. For example, instead of parallel vertical sinusoidal gratings, a test pattern may employ parallel horizontal gratings, oblique parallel gratings, radially-oriented pie slices, or a checkerboard made up of alternating contrasting boxes. Other examples include circular patterns drifting toward the center or toward the periphery, radially-oriented windmills, and test patterns that are presented only in a section of the screen and blocked elsewhere. Any variation of the above test patterns can be optionally combined with a fixation target, which could be a dot, circle, cross, alphanumeric character, or image on which the patient attempts to maintain fixation despite the spatially translating test pattern.

According to another aspect of the present disclosure, a method for using the system 100 to analyze a patient's ocular health is provided. In particular, a patient's ocular health can be analyzed through determining the patient's contrast sensitivity, spatial acuity, temporal acuity, and/or speed facility and monitoring that determined level over time for any changes and/or comparing the determined level to an average or collected level of the general population.

In some embodiments, the operation of testing system 100 preferably starts with optimizing the position of the patient 108 by adjusting the chin/head rest (not shown), chair, and/or table or platform on which the display device 102 sits. The position of camera 106 can also be adjusted for optimal observation of the pupil of the patient 108 being evaluated. Further, the position of the illuminating device 104, e.g., infrared light source(s), may be optimized, either for specular or off-angle illumination. In addition, the display device 102 can also be optimized.

The camera 106 can be optimized manually by the user or by automated protocols to adjust for factors that can impact the ability of the camera to identify and monitor the pupil, such as skin pigmentation, lighting conditions, eyelash length, iris color, etc. In one embodiment, the automated protocols can take still images (snapshots) for optimization using the following steps:

a. Optimize gain of camera according to patient skin tone and lighting characteristics. In one embodiment, this is done by taking a snapshot of the face of the patient 108 with a default gain, adjusting the gain, taking a snapshot with the adjusted gain, adjusting the gain, and repeating this process until the image reaches a pre-determined optimized intensity profile. This profile would examine the image for a clearly distinguishable pupil by counting the number of pixels darker than a threshold (for off-axis illumination, where the pupil is very black) and matching to a standardized value for the typical size of a pupil and testing if these dark pixels form a contiguous round object, consistent with what we expect from a pupil.

b. Optimize pupil-identification of the camera according to the iris characteristics, such as color, shape, and size, of the patient 108. Several methods exist to determine the location of the pupil. At this step, slow methods used in certain embodiments can be used to determine constants which will improve the accuracy of faster methods used during experimentation, such as determining the radius of the pupil for later identification of the pupil by Hough circle transform related methods.

If the testing takes place in a dark environment, the optimization is preferably performed in the same condition. In other embodiments, only some of these optimization steps are performed. In yet other embodiments, none of these optimizations are performed.

Once system 100 is optimized or calibrated or is ready for testing without optimization, various protocols can be implemented, depending on the desired test. One protocol can test for a patient's contrast threshold to a defined spatiotemporal stimulus, another protocol can test for the patient's spatial acuity, another can test for the patient's temporal acuity, and yet another can test for the patient's speed facility. Any of those four parameters can have any of several properties estimated, such as their response gain (the relative benefit to visual perception for a change in the given parameter), critical values defining their peak sensitivity, activation threshold, or any other perceptually relevant value. Furthermore, any of the prior can be tested simultaneously allowing for the determination of possible interdependencies.

That is, there can be five parameters of the stimulus gratings that can be changed: contrast (peak to peak intensity variation), spatial frequency (visual angle per sinusoid cycle), temporal frequency (local rate of change), speed (global rate of change), and direction of movement. Note that speed, spatial frequency, and temporal frequency are interdependent so that knowing any two you can calculate the third. Each of the five parameters can be combined to determine whether a stimulus is perceivable by the subject. For image speed, temporal frequency, and spatial frequency incremental increases improve our ability to detect them up until some critical stimulus parameter value, above which further increases are obfuscating. For example, a patient can be tested to determine some high and low spatiotemporal frequencies beyond which they are unable to perceive stimuli. Increasing contrast, on the other hand, always improves stimulus perception albeit with diminishing benefits. In one embodiment, the system 100 estimates the parameters of a mathematical model fully describing the subject's dependencies on the five stimulus parameters mentioned. In alternative embodiments, certain model parameters are constrained allowing for faster, more directed estimation of specific model parameters. In some embodiments, the parameters of the mathematical model represent the rates at which perception increases relative to stimulus parameters (gains), the values of stimulus parameters beyond which further increases limit perception (critical values), and/or the values where perception is detectable half the time (thresholds). One or any combination of model parameters can be tested and corresponding estimates of that parameter can be determined as described according to the various embodiments of the present disclosure.

In one embodiment, any combination of eight values can be directly determined: contrast gain/threshold, spatial frequency gain/critical value, temporal frequency gain/critical value, and speed gain/critical value. For instance, in order to estimate contrast gain, all other parameters should be defined (contrast threshold, spatial frequency gain/critical value, temporal frequency gain/critical value, and/or speed gain/critical value). In another embodiment, if all the values are desired, no constraints may be applied.

A high level of contrast sensitivity can detect very small differences in luminance. A high level of spatial acuity allows for the detection of smaller sinusoid widths. A high temporal acuity allows for detection of more extreme local sinusoid oscillations. A high speed facility allows for detection of more extreme spatial translation of the visual scene. In certain embodiments, any or all of these alone or in combination can be estimated. Certain diseases or stages of a particular disease may have reduced contrast sensitivity, spatial acuity, temporal acuity, or speed facility or other permutations therein and allow for their diagnosis.

During testing, there can be ambient lighting or it can be dark. In the preferred embodiment, one eye is tested at a time with the fellow eye occluded. If the patient's eye will be covered, the optimization is preferably performed with the patient having the cover as it would be for testing. In another embodiment, neither eye is occluded so both eyes are tested at the same time. In another embodiment illustrated in FIGS. 1B and 2B, neither eye is occluded but a rotatable, opaque divider 118 can be used to isolate testing to one eye at a time.

Figure 4A:
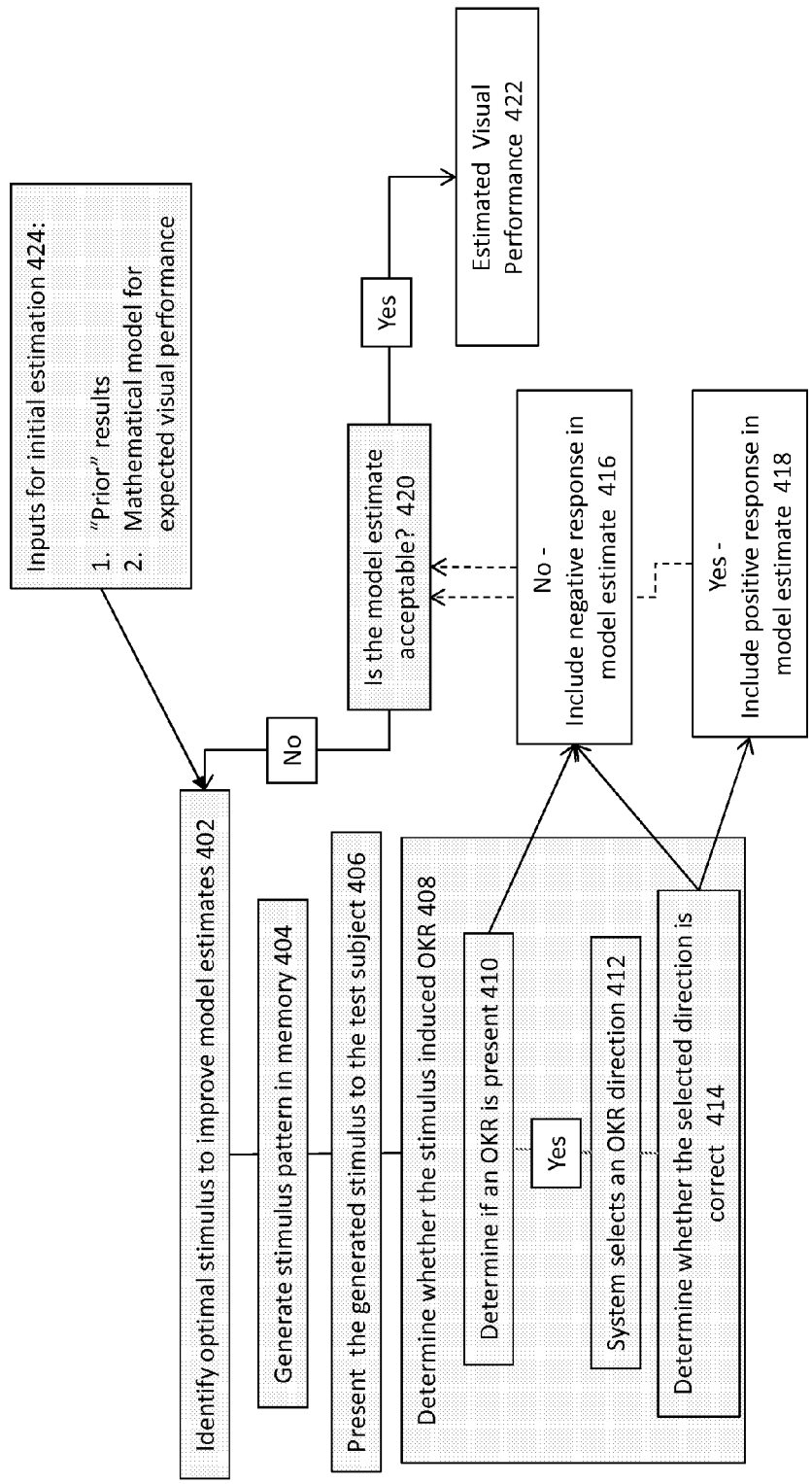
FIG. 4A is a flow chart illustrating the general protocol to estimate visual performance of a test subject according to the aspects of the present disclosure.

FIG. 4A illustrates a method of determining an estimate of visual performance implemented in accordance with an embodiment of the present disclosure once the system is ready for testing. Depending on the initial visual stimulus chosen, the fast and slow phases of the OKR can be induced and identified. If it is induced, this correct response is included in the model estimate. If the chosen initial visual stimulus does not induce an OKR or the OKR direction is incorrectly identified, the model estimate is updated to include this incorrect response. The process is repeated until a sufficiently good estimate of visual function is achieved. In one embodiment, a machine learning algorithm is used to pick the initial conditions of the test and to adaptively choose subsequent testing conditions, e.g., contrasts, speed, temporal frequency, and spatial frequency, to identify the patient's visual function. This allows for rapid convergence of the initial model estimate to the final estimate of visual function. In one embodiment, the machine learning algorithm receives the benefit of knowing beforehand various visual performance statistics of the population.

Referring to FIG. 4A, in step 402, an initial visual stimulus is selected based on the chosen model of visual performance and prior knowledge, which takes into consideration certain factors that are specific to the patient, as provided in further detail below. The estimated model can be for contrast sensitivity, spatial acuity, temporal acuity, speed facility, or all four. If only the patient's contrast sensitivity is being tested, the stimulus spatial frequency, temporal frequency, and speed of the visual stimulus are held constant, and the contrast between the gratings is altered. If only the patient's spatial acuity is being tested, the stimulus contrast, temporal frequency, and speed are held constant while the spatial frequency is changed. If only temporal acuity is being tested, the stimulus contrast, spatial frequency, and speed are held constant while the temporal frequency is changed. If only speed facility is being tested, the stimulus contrast, spatial frequency, and temporal frequency are held constant while the speed is changed. Any of these measures can be estimated in combination as well. For example, if both contrast sensitivity and spatial acuity are being tested simultaneously, the speed and temporal frequency remain constant while both the spatial frequency and contrast are altered. If all model parameters are being tested, then all stimulus parameters can be altered. As such, the description below does not specify the factor being estimated, e.g., contrast sensitivity, spatial acuity, temporal acuity, or speed facility, as this will depend on the test. Thus, in a test of a specific element of visual function, the first stimulus selected by the system 100 for presentation to the patient is that which is expected to most improve an estimate of that element's impact on the subject's visual performance. The constrained features of the stimulus are determined, for example, by estimating the optimal values to elicit a response, which can be determined from previous tests on general population patients. The initial stimulus can be determined using statistical methods such as Bayes' theorem to choose the most informative stimulus parameters to test. In some embodiments, the statistical determinations can be improved with the following pieces of information: (1) the current best-guess probability that a given patient has a particular level of visual function, known as the "prior"; and/or (2) a predictive model for visual performance/function. This information serves as the basis for the initial estimation as shown by step 424 in FIG. 4A.

In one embodiment, the "prior" from above can be provided by a look-up table describing the population's likelihood of having a given level of visual performance. The estimate can be further refined by using patient information which would inform the search such as gender, age, and intraocular pressure or other known risk factors. These factors can be determined empirically as part of a normative database of age-matched healthy test subjects or from the patient's test history. The "prior" can also be the posterior distribution resulting from updating the previous test's prior based on Bayes' rule.

The predictive model can reflect the fact that psychometric tests near threshold have associated error rates. Modeling these error rates in system 100 can improve testing efficiency. In one embodiment, the acceptable form to model these error rates is a psychometric function (logarithmic or linear). Such a function would allow for the input of at least two variables: one representing the patient's visual capability, and the other a stimulus property. The function would return a probability estimate of the patient correctly perceiving the stimulus.

In step 402, the current estimate of visual performance can be used to identify the next stimulus. In the preferred embodiment, this occurs by calculating the expected information gained by testing possible stimuli. The next stimulus which is generated at step 404 can be a single stimulus predicted to provide the most information about the patient's visual performance. There can be multiple ways to value the information gained from a given stimulus. In one embodiment, a stimulus is selected that results in an expected updated model estimate with the lowest mean entropy. Because entropy represents uncertainty in our estimate of visual performance, this approach may choose the stimulus which is expected to most improve our estimate certainty.

Once a stimulus, is chosen, the system 100 can generate a test pattern comprising a series of frames in step 404 of FIG. 4A. The test pattern can be stored in the memory or video memory of computer system 110. In the preferred embodiment, each frame comprises a sinusoidally modulated grating. Successive frames are spatially shifted relative to adjacent frames proportional to the desired translation speed and direction of the grating.

Referring to FIG. 4A, in step 406, the test pattern is presented to the patient for a time period, such as 2-7 seconds (2 seconds for a high test speed, 7 seconds for sensitivity and high accuracy per number of trials, and 4 seconds for a balance of test speed, accuracy, and sensitivity), which constitutes a single trial. A test is made up of several iterations of trials, as shown by FIG. 4A, until system 100 determines a patient's estimated visual performance in step 422. For example, after presenting the stimulus to the subject at step 406 it is determined whether the stimulus induced OKR at step 410. If so, then the system 100 selects an OKR direction 412 and determines whether the selected direction is correct at step 414. If the OKR is not present at step 410, then the negative response is included in the model estimate at step 416. If the selected OKR direction at step 414 is correct, then the positive response is included in the model estimate at step 418. If the selected OKR direction at step 414 is not correct, then the negative response is included in the model estimate at step 416. After the positive or negative response is incorporated into the model estimate, the system 100 can determine whether the model estimate is acceptable at step 420.

Figure 6:
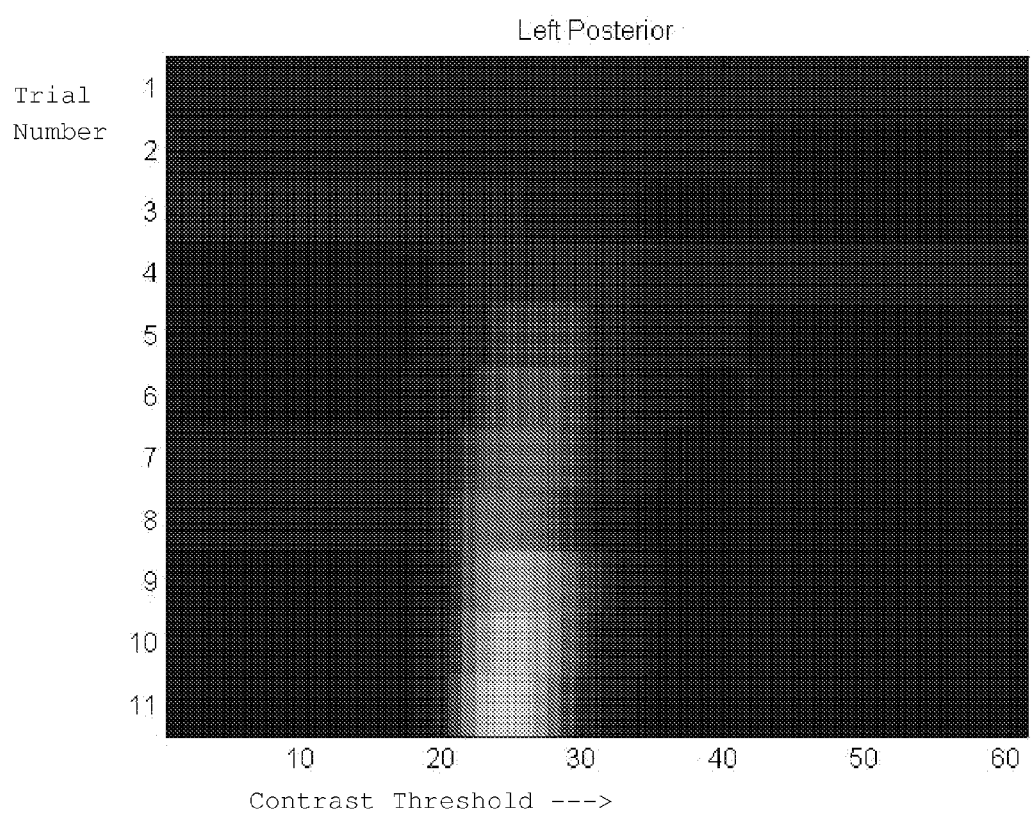
FIG. 6 shows a probability heat map estimating contrast threshold with high statistical probability in 10 trials performed according to the aspects of the present disclosure.

One way a system 100 can determine a patient's visual performance is acceptable, as in step 420 of FIG. 4A, is by determining when the changes in the estimate of threshold are sufficiently small so that further testing does not improve the overall estimate above a certain threshold. This can be done by comparing the current estimate of visual performance with the next estimate of visual performance. An acceptable visual performance estimate occurs when the difference falls within a pre-determined range. In another embodiment, a visual performance estimate is acceptable if system 100 determines that it is within a provided minimum probability. This can occur, for example, within 20 trials, 10 in the right direction, and 10 in the left direction. The number of trials can be varied, with additional trials (40 total trials) providing improved accuracy. In another embodiment sufficient estimate certainty at step 420 can be determined by calculating the entropy of the model parameter probability distributions. In this embodiment experimentation would cease when estimate uncertainty had decreased to a pre-determined level. FIG. 6 shows a probability heat map estimating contrast sensitivity with high statistical probability in 10 trials.

In some embodiments, when the test pattern is presented to the patient in step 406, the direction of movement of the pattern, e.g., left or right, is randomized. Trials can be drawn, without replacement, from a pool consisting of 50% of the frames moving to the right and 50% of the frames moving to the left. In one embodiment, within a continuous trial, the spatiotemporal frequency, speed, and/or contrast of the sinusoid can be modulated to achieve different grating spatial frequencies. In another embodiment, the frames can be frequency chirped to create the illusion of a curved surface, such as one would experience with a rotating cylinder.

During step 406, in one embodiment, system 100 initiates recording from the camera 106, suspends unnecessary background processes, and begins presentation of the stimulus on display device 102. In one embodiment, each of the generated frames is loaded into video memory of computer 110 and displayed on the display device 102 in sequence. In one embodiment, temporal frequencies are constrained to be multiples of the frame duration, such that frames from a single phase shift can be stored, and the frames displayed repeatedly.

In one embodiment, the system 100 is designed to identify the characteristic pupillary movements of an active OKR and adjust the contrast sensitivity based on the results of a previous trial for subsequent trials until an acceptable estimate of model parameters is determined. For estimation of single model parameters this can be done preferably within 25 trials, more preferably within 15 trials, and most preferably within 10 trials. In one embodiment, the entire process of identifying the characteristic pupillary movements and reducing the contrast sensitivity accordingly can be automated. As such, an operator's input or patient's input, such as operator detection of an OKR, is no longer required.

In one embodiment, the video of the patient's pupil movement in response to the stimulus presented in the trial is stored and the recording from the camera 106 is temporarily suspended. After the test pattern for one trial is presented and the video is stored, the system 100 analyzes the stored video to identify the pupil position at each frame in the recorded video from the camera 106, which is preferably recording at 25 frames per second, more preferably running at 30 frames per second, and most preferably at 60 frames per second to determine whether the test pattern of that trial induced OKR in the patient in step 408.

Figure 7:
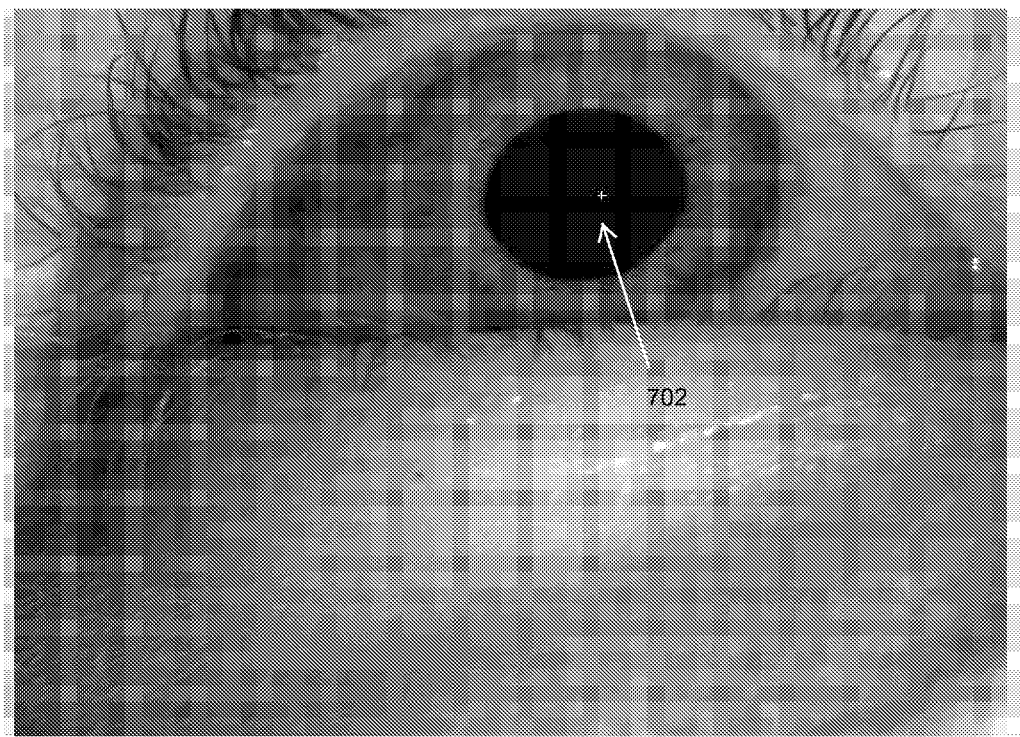
FIG. 7 illustrates an exemplary method to identify the position of a pupil of a test subject according to the aspects of the present disclosure.

In one embodiment, pupil position is identified by system 100 finding the largest area of dark pixels (for off-axis illumination) and marks the central point of these as the pupil's center. FIG. 7 illustrates a pupil of a test subject with crosshair 702 identifying the pupil's center. In another embodiment, the identification process can be further refined by having the operator pre-select an area where the pupil can occur. In yet another embodiment, the process further is improved by relying on the round shape of the pupil. This reliance takes the form of 1) a Hough circle transform test, which involves finding all edges in the image, and then convolving a circle across the image to identify the central point of circles with the proscribed radius or radii or 2) using image segregation techniques to identify contiguous areas with similar shading, and then calculating the ratio of surface area to circumference. Because area=$pi*r^2$ and circumference=$2*pi*r$, the more circular the object is the closer the area divided by the circumference will be to $pi/2$. As such, the object with the most circular shape would have its centroid selected as the pupil's center.

Figure 8:
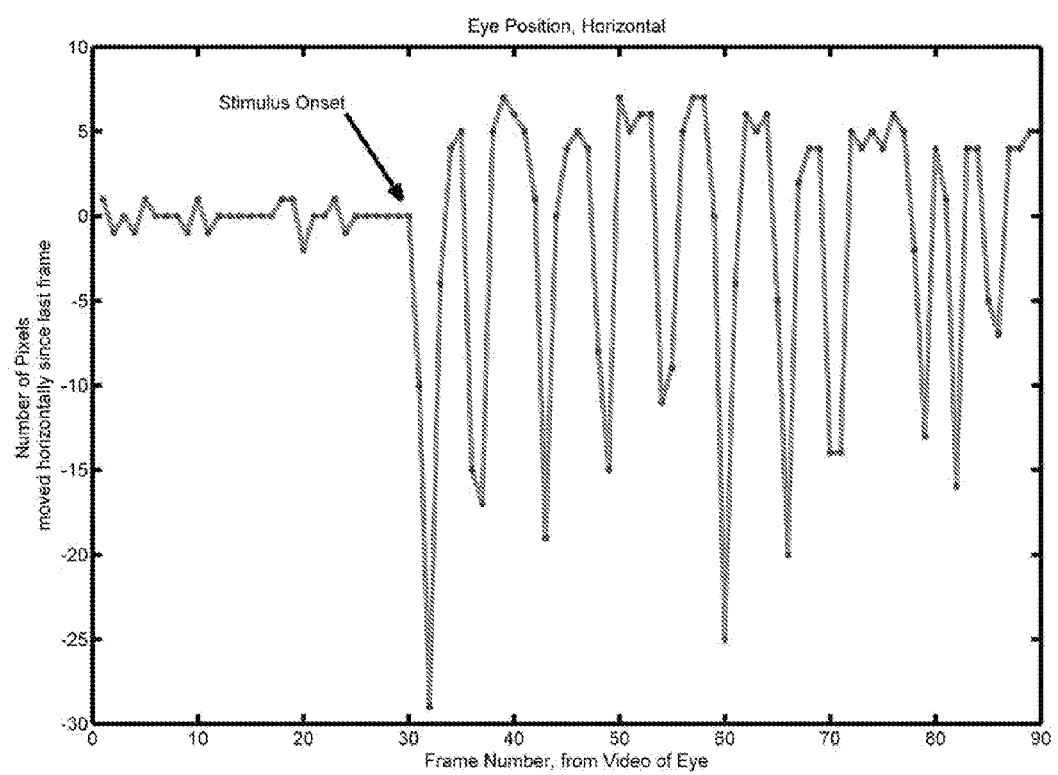
FIG. 8 is an exemplary plot of the horizontal movements of the test subject's eye during the various trials of the test according to the aspects of the present disclosure.

After the pupil position is identified for each image frame of the video recorded by the camera 106, the system 100 can create a frame by frame reconstruction of the pupil positions recorded. Using this frame by frame reconstruction, the horizontal component of the pupil position can be analyzed and movement can be detected. FIG. 8 is a plot of the horizontal movements of the test subject's eye during the various trials of the test.

Because the presented image translates horizontally, this positional history reflects any optokinetic response. In one embodiment, determining whether there was an OKR response is performed by steps 410-414 in FIG. 4A. In step 410, the system 100 first determines whether there was any pupil movement in response to the test pattern presented, regardless of direction. For example, the determining may include calculating the Fourier spectrum of the response and measuring whether a rhythmic movement is present. This could appear as an increase in power of certain frequencies, or as a general decrease in the Fourier spectral entropy. In another embodiment, OKR movement can be detected by the efficacy with which the stimulus was tracked during the slow phase, as measured by the average speed of the pupil movement during the slow phase relative to the speed that would be achieved if the patient's eye was tracking at exactly the stimulus speed. In another embodiment, OKR movement can be detected by looking at the difference in pupil position between each recorded frame. Because OKR is characterized by a slow and fast phase, a recording with an OKR present can contain significantly more small changes in the direction of stimulus movement. Therefore a simple sign test (counting the number of positive and negative pupil position changes between frames) can suffice for a simple OKR detector. When OKR is absent, random eye movements will have a balanced expected number of positive and negative movements. If the system 100 does not detect any movement, the system 100 can use this determination to adjust the next estimate threshold higher. If the system 100 determines there was movement, the system 100 can make a left/right decision based on the horizontal movement trace in step 412. This decision can be based on the fact that there is a slow (tracking) and fast (saccade) phase of an optokinetic reflex (OKR), with the slow phase being in the direction of stimulus movement. The simplest method for determining this is to calculate the difference in horizontal pupil position between each frame. The direction of motion will be associated with many small increases, while the opposite direction will have a smaller number of large jumps. This guess of direction from the analysis software is then passed to a command routine, which grades it as correct or incorrect in step 414. Based on that result, the estimate of the visual performance can be updated.

As shown by step 416, if the guess was incorrect or if no OKR was detected, the system will update the model estimate to include the negative response. If the guess was correct, as shown by step 418, the visual performance estimate will be improved and the system will update the model estimate to include the positive response. In the preferred embodiment, in order to update the model, the system uses Bayes' theorem to translate the current prior probability (the likelihood that any of several models of visual performance represent the patient's true level of visual performance) into a set (the posterior probability) containing the updated model probabilities. In step 420, this set is used to determine a new estimate of visual performance and if this estimate is sufficiently certain the model estimate is deemed to be acceptable (step 422). If this estimate is not deemed to be acceptable, the system returns to step 402, in which the next test stimulus is identified. The time or pause between trials for system 100 to analyze pupil movement and adjust the estimate threshold takes preferably about 1 second. The complete test for one eye to determine a patient's threshold takes preferably less than about 3 minutes, more preferably about 1 minute 30 seconds, and most preferably about 45 seconds.

In another embodiment, the patient's pupil position is monitored and analyzed in real time under infrared lighting 104 by a digital camera 106. In other words, in a real-time embodiment, there would be no pause between trials, i.e., no pause between the presentations of successive stimuli. Essentially, the system 100 would track the eye movements and, if present or absent, immediately change the stimulus according to the adaptive protocol rather than pause and choose a new stimulus for the next trial. As such, the visual stimulus presented to the patient can be constantly changing based on real time data and analysis.

As mentioned above, in step 420, the system 100 determines whether the current model parameter estimate is acceptable. In one embodiment, this is done after the probability distribution of the model parameter has been updated, but before the next stimulus has been presented. The system 100 compares either the current estimate quality to some absolute measure of quality or the expected information gain from the next prior to see if it is sufficiently large to motivate the next trial. The trials continue until the system 100 determines an acceptable model estimate as discussed above. Alternatively, in some embodiments trials would continue until either an acceptable model estimate was reached, or a certain maximum number of trials had been reached, preferably 100 trials, more preferably 50, and most preferably 30. In one embodiment, the system runs until a set number of trials have been reached regardless of the quality of the current estimate.

In one embodiment, the results from the test can be expressed using a mathematical model which accepts as inputs both the stimulus parameters and a set of model parameters that represent the subject's visual ability. This model can be used to determine the probability of a successful response given the stimulus parameters and the current best-guess estimate of the model parameters. Model parameters may represent gains (ratio of benefit in perception to gain in stimulus parameters), critical values (rate at which increasing stimulus parameters has a negative effect), or half-maximums/thresholds. Some models may take the form of contrast or luminal sensitivity curves comprising one or more psychometric functions, possibly in combination with any of the other model features previously described. Psychometric functions may have a sigmoidal form but are not restricted to this shape.

Figure 4B:
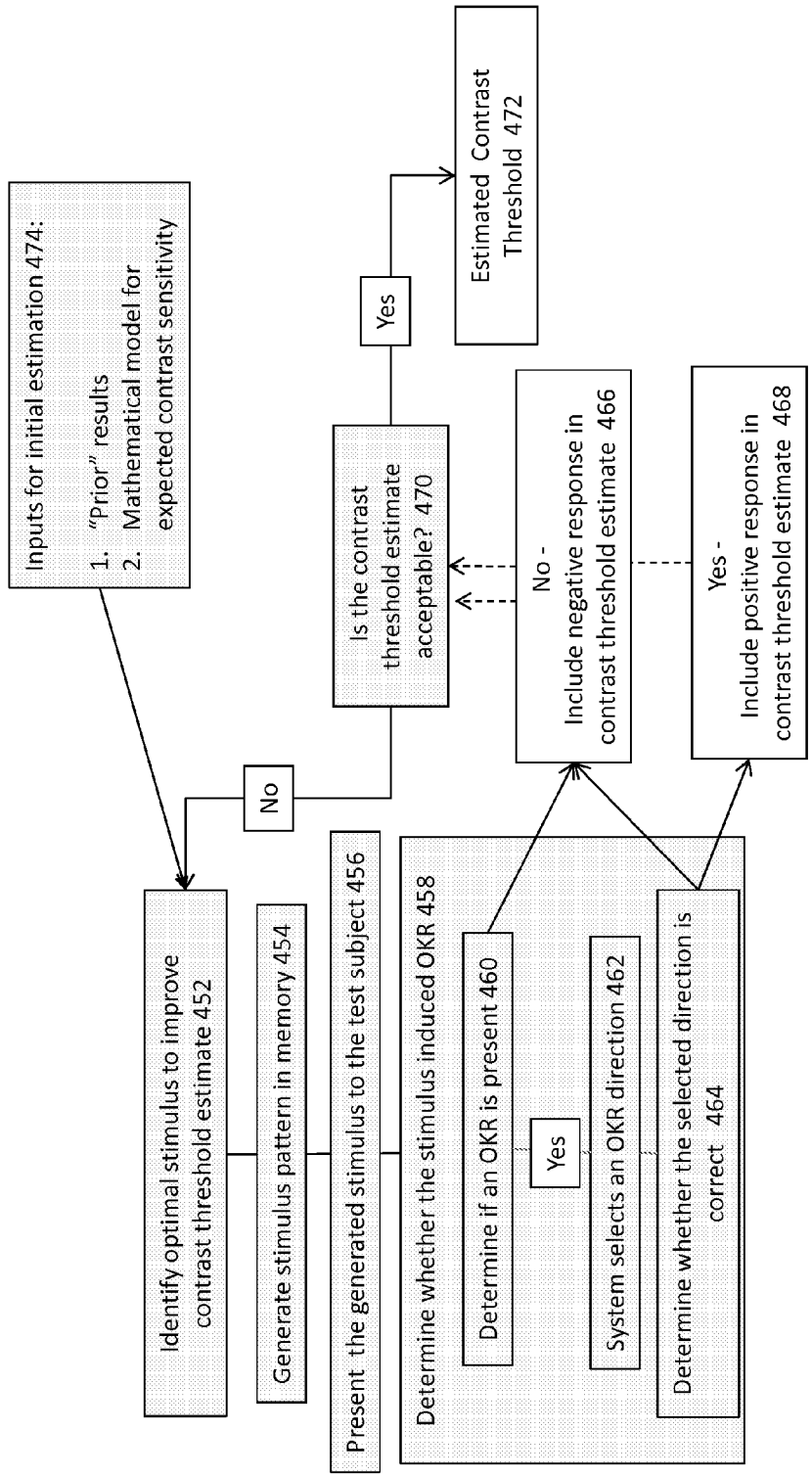
FIG. 4B is a flow chart illustrating one exemplary embodiment to determine contrast threshold of a test subject according to the aspects of the present disclosure.

In one embodiment illustrated in FIG. 4B, the patient's contrast threshold (the point at which they correctly observe the stimulus half of the time) is the only variable in the psychometric function. In this embodiment, the gain (the function's slope, or rate at which additional contrast improves the detection rate) of the contrast portion of the psychometric function can be constrained, and the stimulus spatial frequency, temporal frequency, and speed can be similarly constrained. In other embodiments, the psychometric function can have any combination of gain, half-maximum, critical value, or other parameter types for any stimulus feature including contrast, spatial frequency, temporal frequency, speed, or stimulus light intensity. These parameters can be determined simultaneously (in parallel), with additional time required for each.

In particular, there can be five parameters of the standard stimulus to which a test patient can respond when these parameters are altered: contrast, spatial frequency, temporal frequency, speed, and direction. Psychometric functions can be used to provide a model of behavioral responses to stimulus parameters being tested. These psychometric functions take as inputs both the stimulus parameters and the set of model parameters which represent the visual ability of the subject. In specific protocols any of the stimulus parameters can be defined as constant, allowing their associated model parameters to be ignored. For instance, in an embodiment where a test subject's response to contrast is determined or tested, the speed, temporal frequency, and spatial frequency of the visual stimulus are defined leaving only stimulus contrast to be varied experimentally and the contrast model parameters to be estimated. Preferably, a psychometric function is used as a model for behavioral responses to contrasts above or below the "contrast threshold" which is the point at which the stimulus is correctly observed 50% of the time. This psychometric function's sigmoidal shape relies on two variables, the contrast threshold and the contrast gain. The contrast gain indicates how much improvement in stimulus recognition the patient achieves for a given increase in stimulus contrast. In one embodiment, the gain can be constrained to a constant value. Accordingly, the test determines the patient's contrast threshold when the contrast gain is W, temporal frequency is X, the speed is Y, and the spatial frequency is Z, where W, X, Y, and Z are pre-defined constants.

The method of FIG. 4B parallels the method of FIG. 4A. The method begins at step 452 with identifying optimal stimulus to improve contrast threshold estimate. The first time an estimate is generated at step 452, the estimate may be based on "prior" results and/or a mathematical model. Then, at step 454 a stimulus pattern is generated and presented to the test subject at step 456. At step 458, it is determined whether the stimulus induced OKR. For example, at step 460, it is determined whether OKR is present. If not, then the method proceeds to step 466. If so, then the system selects an OKR direction at step 462 and determines whether the selected direction is correct at step 464. If the direction is correct, then the method proceeds to step 468. If not, then the method proceeds to step 466.

At step 466, the negative response may be included in the contrast threshold estimate. At step 468, the positive response may be included in the contrast threshold estimate. After the estimate is updated, it is determined whether the contrast threshold estimate is acceptable at step 470. If so, then the method terminates at step 472. If not, the method is repeated starting at step 452 with the updated model.

In other embodiments, the contrast gain is not constrained to a specific value. In such an embodiment, all of the steps previously described would be the same. However, during the update of the prior probabilities and determination of stimulus parameters before each stimulus, the current prediction for contrast gain is included in the estimate of the likelihood of a successful OKR at each stimulus contrast. A similar extension of the system can be achieved for speed, temporal frequency, and spatial frequency, so that any or all of the possible parameters could be tested. One difference between contrast and spatial frequency/temporal frequency/speed is that both spatiotemporal frequency and speed are expected to extinguish—there are speeds, temporal frequencies, and spatial frequencies both too low and too high for us to distinguish. This is distinct from contrast, where the benefits of increasing contrast only saturate—they never have a negative effect. In the embodiment modeling spatial frequency and speed, the result can be a pair of psychometric functions, one for the stimulus being attained and one inverted (100% to 0%) for the stimulus's OKR effect being extinguished. In another embodiment, the result can be in a form of an alternative function with similar properties. For instance, a function that achieves the maximum fit to patient data while balancing the number of parameters in the equation can be used. The function preferably includes the property of being very low, rising with some peak slope to a maximal height, and falling with some slope to a minimum. The falling slope can be, but is not required to be, the same as the rising slope. In another embodiment, a plurality of candidate equations or functions can be tested on a variety of test subjects, and one or more equations or functions can selected based on a balance of the goodness of fit with the number of variables.

The method described in FIG. 4A can be implemented to test the other eye, thereby providing two separate model estimates, one for each eye. In addition, the patient can be tested in a dark environment after the patient has readjusted to the dark condition. Depending on testing parameters, additional neutral density filters may be placed between the patient and the monitor to reduce the amount of light to a level that is appropriate for dark-adapted testing. As discussed above, testing in the dark allows for analysis of the more light-sensitive rods. The system 100 adjusts for the change in lighting condition by re-adjusting the parameters of the camera 106 for the darkened screen. Because the camera has low pass filter to block visible light, this adjustment should be minimal. The system 100 will also recalculate the size of the pupil for eye tracking, because it will likely expand during the dark adaptation.

In one embodiment, there can be four sets of model estimates: right eye in ambient lighting, left eye in ambient lighting, right eye in a dark environment, and left eye in a dark environment. These results can be compared with one another or with the patient's historical values for monitoring purposes.

As discussed elsewhere in the application, the steps illustrated in FIG. 4A, particularly the iteration process, can be used to test a patient by varying or keeping constant one or more stimulus parameters: contrast, spatial frequency, temporal frequency, or speed.

In one embodiment, the contrast sensitivity results, as well as results from spatial acuity, temporal acuity, and speed facility, can be used to compare inter-ocular responses in a diagnostic application, such as detecting glaucoma: because glaucoma is associated with decreased contrast sensitivity (higher contrast threshold) and can progress independently in each eye, the eye patching protocol allows us to make comparisons between the two eyes as well as comparisons to a standard population. If either or both eyes are significantly worse than the normal population, then glaucoma may be indicated. The degree of divergence between the two eyes can also be a strong indicator that the eye with the higher contrast threshold (poorer vision) is glaucomatous. Similar comparisons can be used for other ocular diseases, modified slightly according to the expected results present in the tested disease state.

In another embodiment, the contrast sensitivity results, as well as results from spatial acuity, temporal acuity, and/or speed facility, can be used to compare intra-ocular responses in a diagnostic application. An example is also glaucoma detection: by testing at two different adaptation states, we have an internal control for each eye. Research indicates that glaucomatous degeneration differentially affects the high sensitivity rod pathways and low sensitivity cone pathways. In this case, we would predict that a strong divergence between the light- and dark-adapted measures will be suggestive of glaucoma. Inherent in the testing protocol is the "choice" between a temporal to nasal translating stimulus versus a stimulus which moves nasal to temporal. In mice, the direction of this response has been shown to be exclusively dominated by the temporal-nasal direction. Meaning that a leftward moving response would solely drive the optokinetic reflex in the right eye. In humans, who have a stronger binocular component, this complete response segregation does not exist. However response direction preference does exist, and can be used as another metric of glaucoma presence and progression. Similar comparisons can be used for other ocular diseases, modified slightly according to the expected results present in the tested disease state.

Additionally, the embodiments of the present disclosure can provide printed reports of global visual function, eye-specific deficiencies, and risk of tested disease. These printouts may provide, but are not limited to, the following information: (1) details of the raw measurement of contrast sensitivity, spatial acuity, temporal acuity, and/or speed facility (whichever is tested) for that test including the duration of the test, the performance of each eye, an indication of the quality of the estimate, and comparisons among testing conditions and eyes for that test; (2) details of any changes in test performance or comparison parameters when compared to previous tests; (3) details of performance when compared with age-matched control patients, such as reporting a test that deviates more than two standard deviations from the mean test in the age-match population; (4) detailed comparisons between the patient's two eyes (inter-eye); (5) detailed comparisons within each eye between directions tested; (6) the patched state of each eye during individual tests; and (7) details of "disease likelihood" as determined empirically by change in performance, large deviation from the normal population, or both, which can be specific for the diseases tested (i.e. glaucoma, macular degeneration, etc.).

Figure 9:
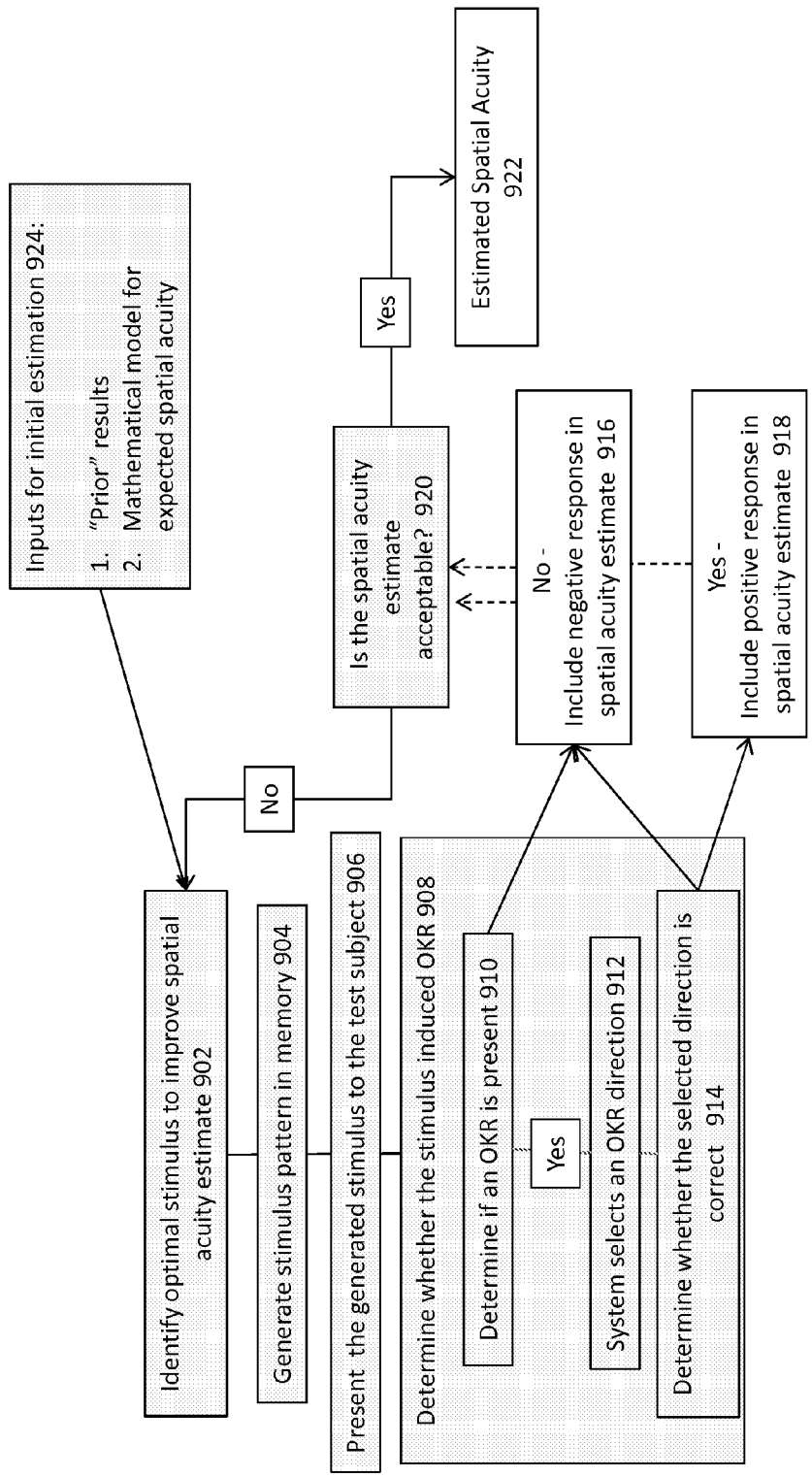
FIG. 9 is flow chart illustrating one exemplary embodiment to determine spatial acuity of a test subject according to the aspects of the present disclosure.

Other embodiments of the present disclosure also contemplated include:

1. Another embodiment uses the software program to choose starting tests, e.g., the series of gratings and their properties (e.g., frequency, speed, contrast);

2. Another embodiment analyzes the eye movement (e.g., OKR) in real time and uses the software program to pick gratings in response to real-time results. In this embodiment the series of trials is replaced by one continuous adaptive trial in which the properties of the gratings are changed in real time according to the presence or absence of an OKR during the most recent frames. With this approach there are no pauses between trials and the time required for an entire test is significantly reduced;

3. Another embodiment measures a subject's spatial acuity using the same algorithms as described above. In this embodiment, stimulus contrast, temporal frequency, and speed are constrained and spatial frequency is varied to determined spatial acuity. Similar to FIG. 4B, FIG. 9 is flow chart illustrating one exemplary embodiment to determine spatial acuity of a test subject according to the aspects of the present disclosure. That is, the method of FIG. 9 begins at step 902 with identifying optical stimulus to improve spatial acuity estimates, generating a stimulus pattern at step 904, presenting the stimulus to the test subject at step 906, determining whether the stimulus induced OKR at step 908 by determining if OKR is present at step 910 and, if so, selecting an OKR direction at step 912 and determining whether the selected direction is correct at step 914, incorporating negative responses into the spatial acuity estimate at step 916, incorporating positive responses into the spatial acuity estimate at step 918, determining whether the estimate is acceptable at step 920, terminating the method at step 922 if acceptable, and repeating the steps beginning at step 902 if not. Similar flow charts for the testing of temporal acuity and speed facility are also contemplated.

4. Another embodiment tests both contrast sensitivity and spatial acuity simultaneously. This method is the same as those described previously with the following variations: (1) the purpose is to determine the contrast sensitivity function of the patient, which is the contrast sensitivity of the patient across a broad range of spatial frequencies; (2) the system can choose both a stimulus contrast and spatial frequency for each trial, as it refines our estimate of the patient's contrast sensitivity function and spatial acuity. or any combination of stimulus parameters.

5. Another embodiment measures rod photoreceptor contrast sensitivity in the dark using a low intensity (dimmer) stimulus. This embodiment requires dark adaptation of the subject for at least 15 minutes so that the high sensitivity rod photoreceptors are not saturated by conditions of bright light. Accordingly, the intensity of the stimulus will be reduced by applying neutral density filters to the monitor to reduce the intensity by at least 3 log units. Testing then follows the same algorithm as described above. This is synonymous with scotopic testing (testing in the light is photopic testing). Photopic tests cone vision "in the light" which we have described already. Mesopic tests cone and rod vision in "dim" light. Scotopic tests rod vision in the dark. In general, the protocol for measuring rod photoreceptor contrast sensitivity in the dark is similar to the protocol for measuring contrast sensitivity in the light. The differences between the two tests are discussed above, including lighting conditions, such as dimmer light and neutral density filter in front of the screen if required as already described in the text. It is also possible other measures of visual performance have rod and cone-specific patterns of variation both under normal conditions and disease states. Therefore, testing of such parameters under dark-adapted conditions are potentially valuable and are contemplated as possible embodiments.

6. Handheld version—controller. Another embodiment uses wireless connectivity between the computer controlling stimulus presentation and a handheld device so that testing setup and completion can be controlled remotely. This removes the need for an operator monitor in the testing room once the patient is positioned.

7. Handheld version—device. Another embodiment uses a handheld device for stimulus presentation. This device could be configured with a handheld camera and infrared light source as well to monitor pupil position. Alternatively, a subjective assessment of OKR induction by an operator could be used in conjunction with the software to assist in determining the need for changes in stimulus presentation. In this embodiment the entire apparatus is portable and can be linked to an operating computer directly with cables or remotely via a wireless connection to allow for operator interface and storage/printing of results.

8. Head mounted version. Another embodiment positions the display device, camera, and infrared light source on a head-mounted device that the subject wears. In this embodiment the entire apparatus is portable and can be linked to an operating computer directly with cables or remotely via a wireless connection to allow for operator interface and storage/printing of results.

9. Another embodiment provides a series of swappable lenses positioned between the subject's eye and the display device (102). With this arrangement the appropriate combination of lenses can be selected so that refractive error is corrected and the patient's glasses do not need to be worn during testing.

10. Another embodiment presents color stimuli instead of or in addition to grayscale stimuli. This embodiment can be used to test and monitor color vision as well as characterizing diseases that selectively affect a subset of color processing pathways.

Figure 10:
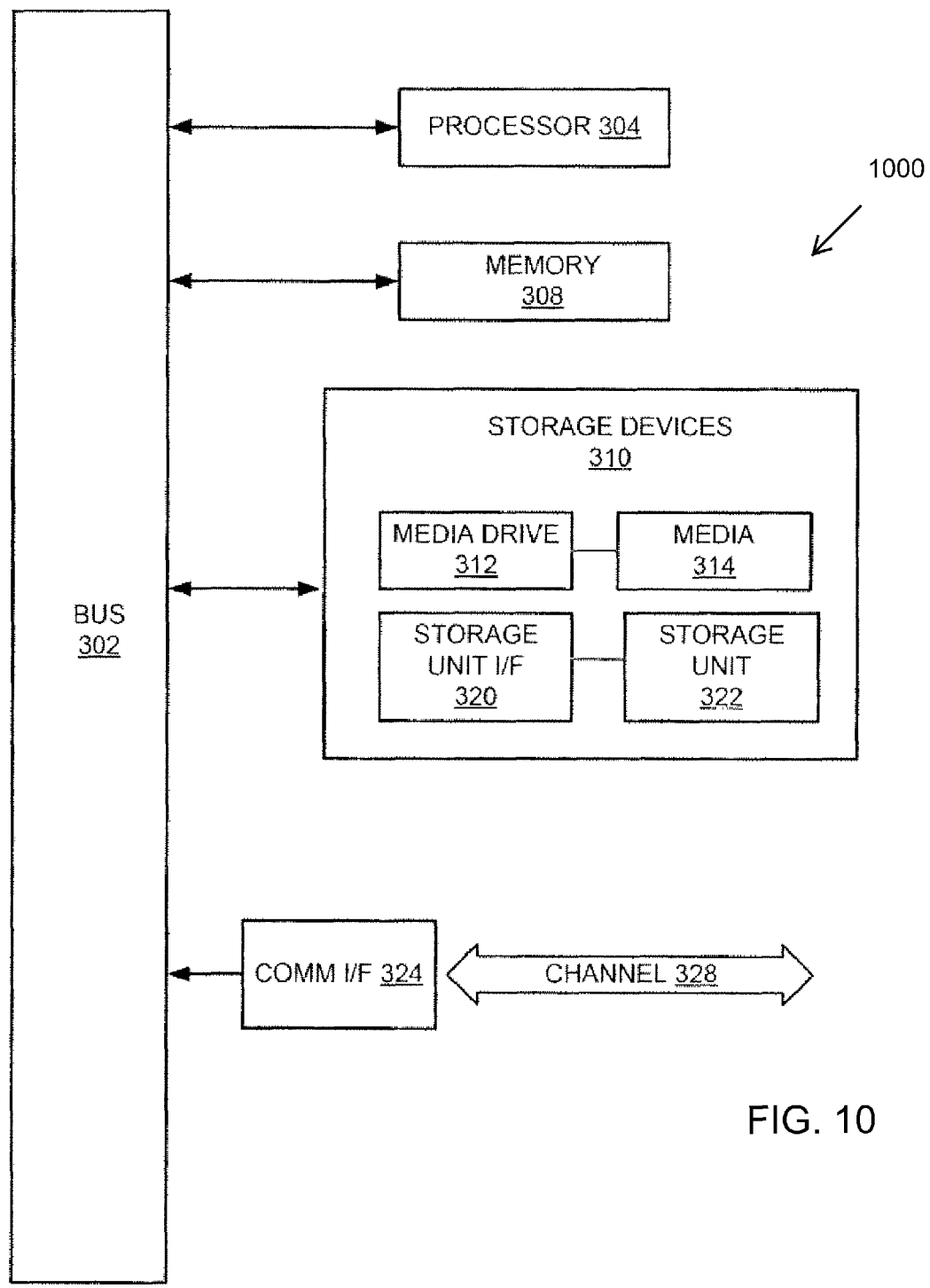
FIG. 10 provides an exemplary computer system for use with the various embodiments of the present disclosure.

As used herein, the term module might describe a given unit of functionality that can be performed in accordance with one or more embodiments of the present invention. As used herein, a module might be implemented utilizing any form of hardware, software, or a combination thereof. For example, one or more processors, controllers, ASICs, PLAs, PALs, CPLDs, FPGAs, GPUs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the invention are implemented in whole or in part using software, in one embodiment, these software elements can be implemented to operate with a computing or processing module capable of carrying out the functionality described with respect thereto. One such example of a computing module is shown in FIG. 10. Various embodiments are described in terms of this example computer system 110. After reading this description, it will become apparent to a person skilled in the relevant art how to implement the invention using other computing modules or architectures.

Referring now to FIG. 10, computer system 110 may represent, for example, computing or processing capabilities found within desktop, laptop and notebook computers; handheld computing devices (PDA's, smart phones, cell phones, palmtops, etc.); mainframes, supercomputers, workstations or servers; or any other type of special-purpose or general-purpose computing devices as may be desirable or appropriate for a given application or environment. Computer system 110 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computer system 110 might include, for example, one or more processors, controllers, control modules, or other processing devices, such as a processor 304. Processor 304 might be implemented using a general-purpose or special-purpose processing engine such as, for example, a microprocessor, controller, or other control logic. In the illustrated example, processor 304 is connected to a bus 302, although any communication medium can be used to facilitate interaction with other components of computer system 110 or to communicate externally.

Computer system 110 might also include one or more memory modules, simply referred to herein as main memory 308. For example, preferably random access memory (RAM) or other dynamic memory, might be used for storing information and instructions to be executed by processor 304. Main memory 308 might also be used for storing temporary variables or other intermediate information during execution of instructions to be executed by processor 304. Computer system 110 might likewise include a read only memory ("ROM") or other static storage device coupled to bus 302 for storing static information and instructions for processor 304.

The computer system 110 might also include one or more various forms of information storage mechanism 310, which might include, for example, a media drive 312 and a storage unit interface 320. The media drive 312 might include a drive or other mechanism to support fixed or removable storage media 314. For example, a hard disk drive, a floppy disk drive, a magnetic tape drive, an optical disk drive, a CD or DVD drive (-R or -RW), or other removable or fixed media drive might be provided. Accordingly, storage media 314 might include, for example, a hard disk, a floppy disk, magnetic tape, cartridge, optical disk, a CD or DVD, or other fixed or removable medium that is read by, written to or accessed by media drive 312. As these examples illustrate, the storage media 314 can include a computer usable storage medium having stored therein computer software or data.

In alternative embodiments, information storage mechanism 310 might include other similar instrumentalities for allowing computer programs or other instructions or data to be loaded into computer system 110. Such instrumentalities might include, for example, a fixed or removable storage unit 322 and an interface 320. Examples of such storage units 322 and interfaces 320 can include a program cartridge and cartridge interface removable memory (for example, a flash memory or other removable memory module) and memory slot, a PCMCIA slot and card, and other fixed or removable storage units 322 and interfaces 320 that allow software and data to be transferred from the storage unit 322 to computer system 110.

Computer system 110 might also include a communications interface 324. Communications interface 324 might be used to allow software and data to be transferred between computer system 110 and external devices. Examples of communications interface 324 might include a modem or soft-modem, a network interface (such as an Ethernet, network interface card, WiMax, IEEE 802.XX or other interface), a communications port (such as for example, a USB port, IR port, RS232 port, Bluetooth, RTM interface, or other port), or other communications interface. Software and data transferred via communications interface 324 might typically be carried on signals, which can be electronic, electromagnetic (which includes optical) or other signals capable of being exchanged by a given communications interface 324. These signals might be provided to communications interface 324 via a channel 328. This channel 328 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 308, storage unit 320, media 314, and channel 328. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computer system 110 to perform features or functions of the present invention as discussed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower ease is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

What is claimed is:

1. A method for determining a visual performance metric of a test subject, the method comprising the steps of:
    estimating, by the processor, a model for at least one visual performance metric;
    identifying, by the processor, a stimulus pattern based, at least in part, on the estimated model, wherein the stimulus pattern comprises sinusoidally-modulated contrast gratings;
    generating, on a display, the stimulus pattern to present the stimulus pattern to the test subject;
    determining, by the processor, an Optokinetic Reflex (OKR) result indicating whether the stimulus pattern induced OKR in the test subject;
    updating, by the processor, the estimated model to incorporate the OKR result; and
    determining, by the processor, whether the updated model is acceptable.

2. The method of claim 1, wherein the sinusoidally-modulated contrast gratings comprise vertically-oriented sinusoidal gratings.

3. The method of claim 1, wherein the sinusoidally-modulated contrast gratings comprise horizontally-oriented sinusoidal gratings.

4. The method of claim 1, wherein the sinusoidally-modulated contrast gratings comprise radially-oriented sinusoidal gratings.

5. The method of claim 1, wherein the sinusoidally-modulated contrast gratings comprise an incrementally increasing or decreasing phase between frames.

6. The method of claim 1, further comprising frequency chirping the sinusoidally-modulated contrast gratings to create a relationship between space or time and a stimulus frequency according to the estimated model.

7. The method of claim 1, wherein the sinusoidally-modulated contrast gratings comprise at least one of an incrementally increasing or decreasing spatial frequency and an incrementally increasing or decreasing temporal frequency.

8. The method of claim 1, wherein the stimulus pattern comprises a fixation target comprising at least one of a dot, a circle, a cross, an alphanumeric character, and an image.

9. The method of claim 1, further comprising at least one of identifying glaucoma based on the updated model, monitoring changes in glaucoma based on the updated model, determining changes in visual function after glaucoma surgery based on the updated model, monitoring cataracts based on the updated model, screening for selecting patients for future multifocal intraocular lens implantation based on the updated model, determining changes in visual function after cataract surgery based on the updated model, determining visual function in macular degeneration based on the updated model, determining changes in visual function after treatment of macular degeneration based on the updated model, determining visual function in diabetic retinopathy based on the updated model, determining changes in visual function after treatment of diabetic retinopathy based on the updated model, determining visual function in disease states of the cornea based on the updated model, determining visual function in optic neuritis based on the updated model, determining non-organic visual loss based on the updated model, determining visual function in instances of genetic or acquired disease of the brain or eye based on the updated model, and confirming a subjective measurement of visual function based on the updated model.

10. A method for determining a visual performance metric of a test subject, the method comprising the steps of:

estimating, by the processor, a model for at least one visual performance metric, wherein the at least one visual performance metric comprises at least one of contrast sensitivity, spatial acuity, temporal acuity, and speed facility;

identifying, by the processor, a stimulus pattern based, at least in part, on the estimated model;

generating, on a display, the stimulus pattern to present the stimulus pattern to the test subject;

determining, by the processor, an Optokinetic Reflex (OKR) result indicating whether the stimulus pattern induced OKR in the test subject;

updating, by the processor, the estimated model to incorporate the OKR result; and determining, by the processor, whether the updated model is acceptable.

11. The method of claim 10, wherein the at least one visual performance metric comprises contrast sensitivity, and wherein identifying the stimulus pattern comprises identifying a stimulus pattern comprising a constant spatial frequency, temporal frequency, and speed, and wherein a contrast between gratings of the stimulus pattern is variable between frames.

12. The method of claim 10, wherein the at least one visual performance metric comprises spatial acuity, and wherein identifying the stimulus pattern comprises identifying a stimulus pattern comprising a constant stimulus contrast, temporal frequency, and speed, and wherein a spatial frequency of the stimulus pattern is variable between frames.

13. The method of claim 10, wherein the at least one visual performance metric comprises temporal acuity, and wherein identifying the stimulus pattern comprises identifying a stimulus pattern comprising a constant stimulus contrast, spatial frequency, and speed, and wherein a temporal frequency of the stimulus pattern is variable between frames.

14. The method of claim 10, wherein the at least one visual performance metric comprises speed facility, and wherein identifying the stimulus pattern comprises identifying a stimulus pattern comprising a constant stimulus contrast, spatial frequency, and temporal frequency, and wherein a speed of the stimulus pattern is variable between frames.

15. The method of claim 10, further comprising at least one of identifying glaucoma based on the updated model, monitoring changes in glaucoma based on the updated model, determining changes in visual function after glaucoma surgery based on the updated model, monitoring cataracts based on the updated model, screening for multifocal intraocular lens implantation based on the updated model, determining changes in visual function after cataract surgery based on the updated model, determining visual function in macular degeneration based on the updated model, determining changes in visual function after treatment of macular degeneration based on the updated model, determining visual function in diabetic retinopathy based on the updated model, determining changes in visual function after treatment of diabetic retinopathy based on the updated model, determining visual function in disease states of the cornea based on the updated model, determining visual function in optic neuritis based on the updated model, determining non-organic visual loss based on the updated model, determining visual function in instances of genetic or acquired disease of the brain or eye based on the updated model, and confirming a subjective measurement of visual function based on the updated model.

16. A method for determining a visual performance metric of a test subject, the method comprising the steps of:

estimating, by the processor, a model for at least one visual performance metric;

identifying, by the processor, a stimulus pattern based, at least in part, on the estimated model;

generating, on a display, the stimulus pattern to present the stimulus pattern to the test subject;

determining, by the processor, an Optokinetic Reflex (OKR) result indicating whether the stimulus pattern induced OKR in the test subject;

updating, by the processor, the estimated model to incorporate the OKR result;

determining, by the processor, whether the updated model is acceptable; and generating, by the processor, a comparison of the updated model with a second model.

17. The method of claim 16, wherein the step of generating the comparison comprises generating a comparison of interocular response between a right eye and a left eye.

18. The method of claim 16, wherein the step of generating the comparison comprises generating a comparison of intraocular response for at least one of a right eye and a left eye.

19. The method of claim 18, wherein the step of generating the comparison comprises generating a comparison of intraocular response between light and dim conditions.

20. The method of claim 18, wherein the step of generating the comparison comprises generating a comparison of intraocular response between light and dark conditions.

21. The method of claim 18, wherein the step of generating the comparison comprises generating a comparison of intraocular response for a first stimulus pattern of a first direction and a second stimulus pattern of a different second direction.

22. The method of claim 16, wherein the step of generating the comparison comprises generating a comparison of the updated model with a prior model of the test subject.

23. The method of claim 16, further comprising at least one of identifying glaucoma based on the updated model, monitoring changes in glaucoma based on the updated model, determining changes in visual function after glaucoma surgery based on the updated model, monitoring cataracts based on the updated model, screening for multifocal intraocular lens implantation based on the updated model, determining changes in visual function after cataract surgery based on the updated model, determining visual function in macular degeneration based on the updated model, determining changes in visual function after treatment of macular degeneration based on the updated model, determining visual function in diabetic retinopathy based on the updated model, determining changes in visual function after treatment of diabetic retinopathy based on the updated model, determining visual function in disease states of the cornea based on the updated model, determining visual function in optic neuritis based on the updated model, determining non-organic visual loss based on the updated model, determining visual function in instances of genetic or acquired disease of the brain or eye based on the updated model, and confirming a subjective measurement of visual function based on the updated model.

24. An apparatus, comprising:

a memory;

a processor coupled to the memory, wherein the processor is configured to perform the steps of:

estimating, by the processor, a model for at least one visual performance metric;

identifying, by the processor, a stimulus pattern based, at least in part, on the estimated model, wherein the stimulus pattern comprises sinusoidally-modulated contrast gratings;

generating, on a display, the stimulus pattern to present the stimulus pattern to the test subject;

determining, by the processor, an Optokinetic Reflex (OKR) result indicating whether the stimulus pattern induced OKR in the test subject;

updating, by the processor, the estimated model to incorporate the OKR result; and determining, by the processor, whether the updated model is acceptable.

25. The apparatus of claim 24, wherein the sinusoidally-modulated contrast gratings comprise vertically-oriented sinusoidal gratings.

26. The apparatus of claim 24, wherein the sinusoidally-modulated contrast gratings comprise horizontally-oriented sinusoidal gratings.

27. The apparatus of claim 24, wherein the sinusoidally-modulated contrast gratings comprise radially-oriented sinusoidal gratings.

28. The apparatus of claim 24, wherein the sinusoidally-modulated contrast gratings comprise an incrementally increasing or decreasing phase between frames.

29. The apparatus of claim 24, wherein the processor is further configured to perform the step of:

frequency chirping the sinusoidally-modulated contrast gratings to create a relationship between space or time and a stimulus frequency according to the estimated model.

30. The apparatus of claim 24, wherein the sinusoidally-modulated contrast gratings comprise at least one of an incrementally increasing or decreasing spatial frequency and an incrementally increasing or decreasing temporal frequency.

31. The apparatus of claim 24, wherein the stimulus pattern comprises a fixation target comprising at least one of a dot, a circle, a cross, an alphanumeric character, and an image.

32. The apparatus of claim 24, further comprising at least one of identifying glaucoma based on the updated model, monitoring changes in glaucoma based on the updated model, determining changes in visual function after glaucoma surgery based on the updated model, monitoring cataracts based on the updated model, screening for selecting patients for future multifocal intraocular lens implantation based on the updated model, determining changes in visual function after cataract surgery based on the updated model, determining visual function in macular degeneration based on the updated model, determining changes in visual function after treatment of macular degeneration based on the updated model, determining visual function in diabetic retinopathy based on the updated model, determining changes in visual function after treatment of diabetic retinopathy based on the updated model, determining visual function in disease states of the cornea based on the updated model, determining visual function in optic neuritis based on the updated model, determining non-organic visual loss based on the updated model, determining visual function in instances of genetic or acquired disease of the brain or eye based on the updated model, and confirming a subjective measurement of visual function based on the updated model.

33. An apparatus for determining a visual performance metric of a test subject, the apparatus comprising:

a memory; and a processor coupled to the memory, wherein the processor is configured to perform the steps of:

estimating, by the processor, a model for at least one visual performance metric, wherein the at least one visual performance metric comprises at least one of contrast sensitivity, spatial acuity, temporal acuity, and speed facility;

identifying, by the processor, a stimulus pattern based, at least in part, on the estimated model;

generating, on a display, the stimulus pattern to present the stimulus pattern to the test subject;

determining, by the processor, an Optokinetic Reflex (OKR) result indicating whether the stimulus pattern induced OKR in the test subject;

updating, by the processor, the estimated model to incorporate the OKR result; and determining, by the processor, whether the updated model is acceptable.

34. The apparatus of claim 33, wherein the at least one visual performance metric comprises contrast sensitivity, and wherein identifying the stimulus pattern comprises identifying a stimulus pattern comprising a constant spatial frequency, temporal frequency, and speed, and wherein a contrast between gratings of the stimulus pattern is variable between frames.

35. The apparatus of claim 33, wherein the at least one visual performance metric comprises spatial acuity, and wherein identifying the stimulus pattern comprises identifying a stimulus pattern comprising a constant stimulus contrast, temporal frequency, and speed, and wherein a spatial frequency of the stimulus pattern is variable between frames.

36. The apparatus of claim 33, wherein the at least one visual performance metric comprises temporal acuity, and wherein identifying the stimulus pattern comprises identifying a stimulus pattern comprising a constant stimulus contrast, spatial frequency, and speed, and wherein a temporal frequency of the stimulus pattern is variable between frames.

37. The apparatus of claim 33, wherein the at least one visual performance metric comprises speed facility, and wherein identifying the stimulus pattern comprises identifying a stimulus pattern comprising a constant stimulus contrast, spatial frequency, and temporal frequency, and wherein a speed of the stimulus pattern is variable between frames.

38. The apparatus of claim 33, wherein the processor is further configured to perform the step of identifying glaucoma based on the updated model, monitoring changes in glaucoma based on the updated model, determining changes in visual function after glaucoma surgery based on the updated model, monitoring cataracts based on the updated model, screening for multifocal intraocular lens implantation based on the updated model, determining changes in visual function after cataract surgery based on the updated model, determining visual function in macular degeneration based on the updated model, determining changes in visual function after treatment of macular degeneration based on the updated model, determining visual function in diabetic retinopathy based on the updated model, determining changes in visual function after treatment of diabetic retinopathy based on the updated model, determining visual function in disease states of the cornea based on the updated model, determining visual function in optic neuritis based on the updated model, determining non-organic visual loss based on the updated model, determining visual function in instances of genetic or acquired disease of the brain or eye based on the updated model, and confirming a subjective measurement of visual function based on the updated model.

39. An apparatus for determining a visual performance metric of a test subject, the apparatus comprising:

a memory; and a processor, wherein the processor is configured to perform the steps of:

estimating, by the processor, a model for at least one visual performance metric;

identifying, by the processor, a stimulus pattern based, at least in part, on the estimated model;

generating, on a display, the stimulus pattern to present the stimulus pattern to the test subject;

determining, by the processor, an Optokinetic Reflex (OKR) result indicating whether the stimulus pattern induced OKR in the test subject;

updating, by the processor, the estimated model to incorporate the OKR result;

determining, by the processor, whether the updated model is acceptable; and generating, by the processor, a comparison of the updated model with a second model.

40. The apparatus of claim 39, wherein the step of generating the comparison comprises generating a comparison of inter-ocular response between a right eye and a left eye.

41. The apparatus of claim 39, wherein the step of generating the comparison comprises generating a comparison of intra-ocular response for at least one of a right eye and a left eye.

42. The apparatus of claim 39, wherein the step of generating the comparison comprises generating a comparison of intra-ocular response between light and dim conditions.

43. The apparatus of claim 39, wherein the step of generating the comparison comprises generating a comparison of intra-ocular response between light and dark conditions.

44. The apparatus of claim 39, wherein the step of generating the comparison comprises generating a comparison of intra-ocular response for a first stimulus pattern of a first direction and a second stimulus pattern of a different second direction.

45. The apparatus of claim 39, wherein the step of generating the comparison comprises generating a comparison of the updated model with a prior model of the test subject.

46. The apparatus of claim 39, wherein the processor is further configured to perform the step of identifying glaucoma based on the updated model, monitoring changes in glaucoma based on the updated model, determining changes in visual function after glaucoma surgery based on the updated model, monitoring cataracts based on the updated model, screening for multifocal intraocular lens implantation based on the updated model, determining changes in visual function after cataract surgery based on the updated model, determining visual function in macular degeneration based on the updated model, determining changes in visual function after treatment of macular degeneration based on the updated model, determining visual function in diabetic retinopathy based on the updated model, determining changes in visual function after treatment of diabetic retinopathy based on the updated model, determining visual function in disease states of the cornea based on the updated model, determining visual function in optic neuritis based on the updated model, determining non-organic visual loss based on the updated model, determining visual function in instances of genetic or acquired disease of the brain or eye based on the updated model, and confirming a subjective measurement of visual function based on the updated model.

* * * * *